(12) United States Patent
Sawa et al.

(10) Patent No.: US 9,597,436 B2
(45) Date of Patent: Mar. 21, 2017

(54) ADVANCED HEART FAILURE TREATMENT MATERIAL AS MYOCARDIAL/CARDIOVASCULAR REGENERATION DEVICE

(71) Applicants: Osaka University, Suita-shi (JP); Nipro Corporation, Osaka-shi (JP); Ono Pharmaceutical Co., Ltd., Osaka-shi (JP)

(72) Inventors: Yoshiki Sawa, Suita (JP); Shigeru Miyagawa, Suita (JP); Satsuki Fukushima, Suita (JP); Atsuhiro Saito, Suita (JP); Yoshiki Sakai, Sasayama (JP); Kazuhisa Matsuda, Osaka (JP); Takayuki Maruyama, Mishima-gun (JP)

(73) Assignees: Osaka University, Suita-shi (JP); Nipro Corporation, Osaka-shi (JP); Ono Pharmaceutical Co., Ltd., Osaka-shi (JP)

( * ) Notice: Subject to any disclaimer, the term of this patent is extended or adjusted under 35 U.S.C. 154(b) by 0 days.

(21) Appl. No.: 14/429,565

(22) PCT Filed: Sep. 13, 2013

(86) PCT No.: PCT/JP2013/074948
§ 371 (c)(1),
(2) Date: Mar. 19, 2015

(87) PCT Pub. No.: WO2014/046065
PCT Pub. Date: Mar. 27, 2014

(65) Prior Publication Data
US 2015/0231312 A1    Aug. 20, 2015

(30) Foreign Application Priority Data
Sep. 21, 2012    (JP) .................... 2012-208799

(51) Int. Cl.
*A61K 31/16* (2006.01)
*A61K 31/4406* (2006.01)
(Continued)

(52) U.S. Cl.
CPC ............ *A61L 31/16* (2013.01); *A61K 9/0024* (2013.01); *A61K 9/16* (2013.01); *A61K 31/343* (2013.01);
(Continued)

(58) Field of Classification Search
CPC .............. A61K 31/343; A61K 31/4406; A61K 9/0024; A61K 9/16; A61L 2300/412; A61L 2430/20; A61L 31/148; A61L 31/16
See application file for complete search history.

(56) References Cited

U.S. PATENT DOCUMENTS

| 5,480,998 A | 1/1996 | Hamanaka et al. |
| 5,702,343 A | 12/1997 | Alferness |

(Continued)

FOREIGN PATENT DOCUMENTS

| JP | 2004-503294 A | 2/2004 |
| JP | 2008500881 A | 1/2008 |

(Continued)

OTHER PUBLICATIONS

Yoichiro, Hirata, et al., "A synthetic prostacyclin agonist, ONO-1301, ameliorates ventricular remodeling after acute myocardial infarction via upregulation of HGF in rat", Biomedicine & Aging Pathology, 2011, pp. 90-96, vol. 1, No. 2.
(Continued)

*Primary Examiner* — Aradhana Sasan
(74) *Attorney, Agent, or Firm* — The Webb Law Firm

(57) ABSTRACT

Provided is an advanced heart failure treatment material, as a myocardial/cardiovascular regeneration device, that self-assembles, which can improve the universality and be used
(Continued)

in an emergency by commercialization with no need of cell-culturing (cell-free) by controlling stem cells, and has a high therapeutic effect on the fundamental treatment of intractable cardiovascular diseases, in particular, advanced heart failure, in which not only the saving of lives but also improving the patient's quality of life (QOL) are urgent issues. The advanced heart failure treatment material includes a pharmaceutical agent, an agent holding for the pharmaceutical agent, and a myocardial support device.

20 Claims, 6 Drawing Sheets

(51) Int. Cl.
    A61K 31/343    (2006.01)
    A61K 9/16      (2006.01)
    A61K 9/00      (2006.01)
    A61L 31/14     (2006.01)
    A61L 31/16     (2006.01)

(52) U.S. Cl.
    CPC ........ *A61K 31/4406* (2013.01); *A61L 31/148* (2013.01); *A61L 2300/412* (2013.01); *A61L 2430/20* (2013.01)

(56) References Cited

U.S. PATENT DOCUMENTS

| | | | |
|---|---|---|---|
| 6,046,233 | A | 4/2000 | Kasukawa et al. |
| 6,425,856 | B1 | 7/2002 | Shapland et al. |
| 6,730,016 | B1 | 5/2004 | Cox et al. |
| 6,902,522 | B1 | 6/2005 | Walsh et al. |
| 7,545,715 | B2 | 6/2009 | Ueki |
| 8,617,614 | B2 | 12/2013 | Sakai et al. |
| 8,771,734 | B2 | 7/2014 | Tabata |
| 2005/0267556 | A1 | 12/2005 | Shuros et al. |
| 2006/0140916 | A1 | 6/2006 | Siani-Rose et al. |
| 2008/0107703 | A1 | 5/2008 | Tabata et al. |
| 2010/0323026 | A1* | 12/2010 | Sakai ............. A61K 31/4406 424/501 |

FOREIGN PATENT DOCUMENTS

| | | | |
|---|---|---|---|
| JP | 2008137975 | A | 6/2008 |
| JP | 2008520748 | A | 6/2008 |
| JP | 2008161346 | A | 7/2008 |
| JP | 4582549 | B2 | 9/2010 |
| WO | 9626721 | A1 | 9/1996 |
| WO | 0002500 | A1 | 1/2000 |
| WO | 0185061 | A2 | 11/2001 |
| WO | 0195832 | A2 | 12/2001 |
| WO | 2004032965 | A1 | 4/2004 |
| WO | 2004082657 | A1 | 9/2004 |
| WO | 2006085653 | A1 | 8/2006 |
| WO | 2008047863 | A1 | 4/2008 |

OTHER PUBLICATIONS

Yoichiro, Hirata, et al., "Synthetic prostacycline agonist, 0N0-1301, ameliorates left ventricular dysfunction and cardiac fibrosis in cardiomyopathic hamsters", Biomedicine & phamacotherapy, 2009, pp. 781-786, vol. 63, No. 10.

Hayashi, K., et al., "Modulation of anti-glomerular basement membrane nephritis in rats by 0N0-1301, a non-prostanoid prostaglandin I2 mimetic compound with inhibitory activity against thromboxane A2 synthase", 1997, pp. 73-82, vol. 73, No. 1.

The Japanese Association for Thoracic Surgery, Report of Cardiac Surgery Academic Study Results, 2008.

Sawa, Yoshiki, et al., "Tissue Engineered Myoblast Sheets Improved Cardiac Function Sufficiently to Discontinue LVAS in a Patient with DCM: Report of a Case", Surg Today, 2012, vol. 42, pp. 181-184.

Beltrami, Antonio, et al., "Adult Cardiac Stem Cells Are Mulipotent and Support Myocardial Regeneration", Cell, Sep. 19, 2003, vol. 114, pp. 763-776.

Oh, Hidemasa, et al., "Cardiac Progenitor Cells from Adult Myocardium: Homing, Differentiation, and Fusion After Infarction", PNAS, Oct. 14, 2003, vol. 100, No. 21, pp. 12313-12318.

Laugwitz, Karl-Ludwig, et al., "Post-Natal isl1+ Cardioblasts Enter Fully Differentiated Cardiomyocyte Lineages", Nature, Feb. 10, 2005, vol. 433, pp. 647-653.

Smart, Nicola, et al., "De novo Cardiomyocytes From Within the Activated Adult Heart After Injury", Nature, Jun. 30, 2011, vol. 474, pp. 640-644.

Obata, Hiroaki, et al., "Single Injection of a Sustained-Release Prostacyclin Analog Improves Pulmonary Hypertension in Rats", Am J Respir Crit Care Med, 2008, vol. 177, pp. 195-201.

Xu, Qing, et al., "Suppression of Acute Hepatic Injury by a Synthetic Prostacyclin Agonist Through Hepatocyte Growth Factor Expression", AJP—Gastrointest Liver Physiol, 2012, vol. 302, pp. G420-G429.

Sakai, Yoshiki, "Clinical Application to the Regenerative Medicine of Prostaglandins—ONO-1301, It Begins the Tissue Regeneration!", The Cell, 2011, vol. 43, No. 10, pp. 26-35.

Sakai, Yoshiki, "Clinical Application of an Inducer of Biological Regeneration for Local Administration to Diseased Tissues", The Cell, 2012, vol. 44, No. 2, pp. 34-40.

Nakamura, Kazuto, et al., "A Synthetic Small Molecule, ONO-1301, Enhances Endogenous Growth Factor Expression and Augments Angiogenesis in the Ischaemic Heart", Clinical Science, 2007, vol. 112, pp. 607-616.

Iwata, Hiroshi, et al., "Local Delivery of Synthetic Prostacycline Agonist Augments Collateral Growth and Improves Cardiac Function in a Swine Chronic Cardiac Ischemia Model", Life Sciences, 2009, vol. 85, pp. 255-261.

Shirasaka, Tomonori, et al., "A Novel Slow-Release Form of Prostacycline Agonist (ONO-1301) Induces the Secretion of Multiple Growth Factors and Improves Cardiac Function in Rapid-Pacing Induced End-Stage Heart Failure in Canine Heart", ATS 2011 International Conference/American Thoracic Society, 2011, Denver, Colorado.

Shirasaka, Tomonori, et al., "Combined Therapy of Skeletal Myoblast Cell-Sheet Transplantation With Administration of Prostacycline Agonist Makes Left Ventricular Reverse Remodeling on the Impaired Myocardium in Rapid-Pacing Induced End-Stage Heart Failure in Canine Heart", American Heart Association, 2011, Orlando, Florida.

Hirata, Yoichiro, et al., "A Synthetic Prostacyclin Agonist with Thromboxane Synthase Inhibitory Activity, ONO-1301, Protects Myocardium from Ischemia/Reperfusion Injury", European Journal of Pharmacology, 2012, vol. 674, pp. 352-358.

Hata, Hiroki, et al., "Grafted Skeletal Myoblast Sheets Attenuate Myocardial Remodeling in Pacing-Induced Canine Heart Failure Model", The Journal of Thoracic and Cardiovascular Surgery, Oct. 2006, vol. 132, No. 4, pp. 918-924.

Suzuki et al., "A Prostacycline Analog Prevents Myocardial Remodeling in Murine Cardiac Allografts", Int Heart J, Jan. 2012, vol. 53, No. 1, pp. 64-67.

Extended European Search Report for corresponding European Patent Application No. 13838722.0 dated Mar. 3, 2016.

\* cited by examiner (a)

(b)

(c)

(d)

ADVANCED HEART FAILURE TREATMENT MATERIAL AS MYOCARDIAL/CARDIOVASCULAR REGENERATION DEVICE

CROSS-REFERENCE TO RELATED APPLICATIONS

This application is the United States national phase of International Application No. PCT/JP2013/074948 filed Sep. 13, 2013, and claims priority to Japanese Patent Application No. 2012-208799 filed Sep. 21, 2012, the disclosures of which are hereby incorporated in their entirety by reference.

TECHNICAL FIELD

The present invention relates to an advanced heart failure treatment material as a myocardial/cardiovascular regeneration device, and more specifically relates to an advanced heart failure treatment material as a myocardial/cardiovascular regeneration device that can perform myocardial/cardiovascular regeneration by self-assembly, and be an alternative to artificial hearts, a heart transplantation, and a cell transplantation therapy, in advanced heart failure treatment.

BACKGROUND ART

In the cardiovascular area, intractable cardiovascular disease, such as advanced heart failure, is one of the three major national diseases of Japan. In Japan, which faces an aging society unparalleled in the world, the number of patients suffering from advanced heart failure or a severe aneurysm and the medical cost therefore will increase in the future.

A radical therapy for such intractable cardiovascular diseases has not been established and thus it is assumed that the high medical cost will further increase unless this situation is resolved.

Advanced heart failure is the last stronghold in the area of heart diseases. Currently, about twenty two million people suffer from heart failure around the world, and in the United States of America where heart diseases are the top national cause of death, there are approximately 5.7 million patients with 670,000 people newly developing heart failure every year. The cost required for the treatment is said to reach 37.2 billion dollars per year, leading to the increase in the medical cost. Also, among these patients, the number of advanced heart failure patients who are not expected to improve due to treatment using a pharmaceutical agent is assumed to be approximately 100,000 people (the assumed number worldwide is approximately 200,000). In the United States of America, approximately 2,200 heart transplantations are performed per year.

On the other hand, in Japan, the number of operations for ischemic heart diseases among cardiovascular operations performed in the whole country in 2008 was 19,237. With the most standard isolated coronary artery bypass graft (CABG) operation in ischemic heart disease surgery, primary/elective CABG was performed on 14,943 patients and primary/emergent CABG was performed on 2,508 patients (Non-Patent Document 1).

Development/commercialization and industrialization of medical treatment for advanced heart failure have spread worldwide. In order to deal with the increasing number of patients every year, the establishment of a fundamental treatment for advanced heart failure is urgently needed in Japan where there is feeling of despair in a transplantation therapy due to the significantly insufficient number of donors. Also, a cardiovascular/myocardial regenerative remedy that is an alternative to heart transplantation or artificial hearts, and aims for not relying on artificial hearts is predicted to have a large market scale.

In such circumstances, it is conceivable that a regenerative therapy will be a treatment tool having a high potential to advance the treatment for intractable cardiovascular diseases, and will be an industry that leads to huge economic outcomes. Research on tissue transplantation in which cells are assembled into a tissue for transplantation has been conducted in western countries as well as Japan, and efforts are underway for not only tissue regeneration but also organ regeneration. Research for attempting myocardial tissue regeneration using a tissue engineering method by which cells are seeded in a bioabsorbable support, similarly to bones/cartilages, have mainly been conducted worldwide, but a myocardial tissue having a high cell density has not yet been regenerated.

On the other hand, regeneration of myocardial tissues having a high cell density has been realized, using a tissue regeneration technique in which a unique self-myoblast sheet is used, and the effects on improving heart function have been confirmed by transplantation thereof in the preclinical test, leading to the clinical trial (Non-Patent Document 2).

However, even with such a current tissue regeneration technique, myocardial tissue regeneration that can be an alternative to heart transplantation and completely reverse heart dysfunction in addition to achieving emergency use and universal use has not been achieved.

Also, regarding artificial organs/devices that deal with intractable cardiovascular diseases, even though the functionality is improved, biocompatibility is not sufficient yet, and thus technical breakthrough in eternal use has not been achieved. In order to develop a cardiovascular treatment device having further universality hereafter, it is conceivable that establishing a foundation of medical and engineering fields collaborating in a hybrid type industry by integrating bio/regenerative therapy technology into conventional material/device technology as the basic technology is essential in terms of medical industry development and social importance.

PRIOR ART DOCUMENTS

Non-Patent Document

Non-Patent Document 1: The Japanese Association for Thoracic Surgery (Report of Cardiac Surgery Academic Study Results, 2008)
Non-Patent Document 2: Surg. Today, 2012, 42, pp. 181-184.

The present invention is to solve the above-described issues and the object thereof is to provide an advanced heart failure treatment material, as a myocardial/cardiovascular regeneration device, that self-assembles, which can improve the universality and be used in an emergency by commercialization with no need of cell-culturing (cell-free), and has a high therapeutic effect on the fundamental treatment of intractable cardiovascular diseases, in particular, advanced heart failure, in which not only the saving of lives but also improving the patient's quality of life (QOL) are urgent issues, as being an alternative to conventional artificial hearts, heart transplantation therapy, and a self-cell transplantation therapy that includes long-term culturing.

SUMMARY OF THE INVENTION

In order to solve above-described issues, the present inventors have studied, while studying pharmacologic actions of prostaglandins (PGs), focusing on the possibility of PGs inducing the production of various internal regeneration factors based on the similarity of action with the internal regeneration factors. As a result of the studies, the inventors have found that among PGs, agonists for an IP receptor, an $EP_2$ receptor, and an $EP_4$ receptor that facilitate the production of cyclic AMP (cAMP) have a function for facilitating lumen formation under co-culture of normal human umbilical vein endothelial cells (HUVECs) and human dermal fibroblasts (NHDFs). As a result of further studies, they have found that these agonists induce various internal regeneration factors from fibroblasts, smooth muscle cells, vascular endothelial cells, macrophages, and the like. As a result of the studies, an advanced heart failure treatment material has been developed by, for example, selecting a PGI system, as an internal regeneration factor production inducing agent, that is biosynthesized mainly in vascular endothelial cells, selecting a compound (for example, described in WO 2004/032965) that is a selective IP receptor agonist that is a non-PG skeleton oxime (OX) derivative and has a thromboxane (TX) $A_2$ synthetase inhibitory activity additionally, and combining the compound with a predetermined myocardial support device.

Namely, the present invention is an advanced heart failure treatment material comprising a pharmaceutical agent, an agent holding for the pharmaceutical agent, and a myocardial support device.

In one embodiment, the pharmaceutical agent is an internal regeneration factor production inducing agent.

In one embodiment, the internal regeneration factor production inducing agent is a sustained-release preparation.

In one embodiment, the agent holding for the pharmaceutical agent is a sustained-release preparation holding agent.

In one embodiment, the advanced heart failure treatment material of the present invention comprises a sustained-release preparation of an internal regeneration factor production inducing agent, a sustained-release preparation holding agent, and a myocardial support device.

In one embodiment, the sustained-release preparation of the internal regeneration factor production inducing agent constitutes a sheet or spray together with the sustained-release preparation holding agent.

In one embodiment, the sustained-release preparation of the internal regeneration factor production inducing agent is coated to the myocardial support device via the sustained-release preparation holding agent.

In one embodiment, the sustained-release preparation holding agent is a bioabsorbable high-molecular weight compound.

In one embodiment, the bioabsorbable high-molecular weight compound is at least one high-molecular weight compound selected from the group consisting of fibrin, gelatin, collagen, and hyaluronic acid.

In one embodiment, the bioabsorbable high-molecular weight compound is at least one natural high-molecular weight compound selected from the group consisting of fibrin, atelocollagen, and gelatin.

In one embodiment, the sustained-release preparation of the internal regeneration factor production inducing agent is produced using a biodegradable high-molecular weight compound.

In one embodiment, the internal regeneration factor production inducing agent is at least one selected from the group consisting of a prostaglandin $I_2$ agonist, an $EP_2$ agonist, and an $EP_4$ agonist.

In one embodiment, the prostaglandin $I_2$ agonist is a compound indicated by the following general formula (I) or a salt thereof.

[Formula 1]

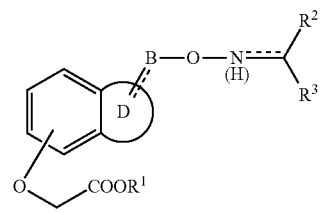
(I)

(in the formula,

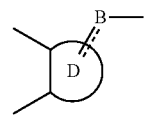

is

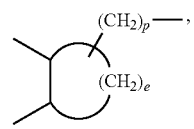
(i)

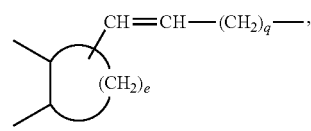
(ii)

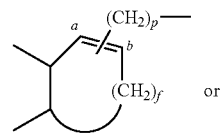
(iii)
or

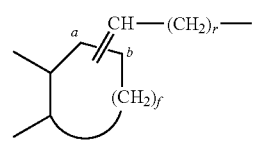
(iv)

(wherein,
$R^1$ is a hydrogen atom or a C1-4 alkyl group,
$R^2$ is (i) a hydrogen atom, (ii) a C1-8 alkyl group that may be branched or form a ring, (iii) a phenyl group or a C4-7 cycloalkyl group, (iv) a 4-7-membered single ring containing one nitrogen atom, (v) a C1-4 alkyl group substituted by a benzene ring or a C1-7 cycloalkyl group, or (vi) a C1-4 alkyl group substituted by a 4-7-membered single ring containing one nitrogen atom, $R^3$ is (i) a C1-8 alkyl group that may be branched or form a ring, (ii) a phenyl group or a C4-7 cycloalkyl group, (iii) a 4-7-membered single ring containing one nitrogen atom, (iv) a C1-4 alkyl group substituted by a benzene ring or a C4-7 cycloalkyl group, or (v) a C1-4 alkyl group substituted by a 4-7-membered single ring containing one nitrogen atom, and e is an integer of 3-5, f is an integer of 1-3, p is an integer of 1-4, q is 1 or 2, and r is an integer of 1-3, provided that in a case where

[Formula 2]

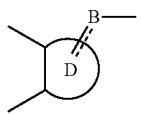

is a group indicated by (iii) or (iv), —$(CH_2)_p$— and =CH—$(CH_2)_r$— are bound to a or b on a ring, and a ring in $R^2$ and $R^3$ may be substituted by one to three C1-4 alkyl groups, C1-4 alkoxy groups, halogen atoms, nitro groups, or trihalomethyl groups).

In one embodiment, the prostaglandin $I_2$ agonist is (E)-[5-[2-[1-phenyl-1-(3-pyridyl)methylideneaminoxy]ethyl]-7,8-dihydronaphthalen-1-yloxy]acetic acid or salt thereof.

In one embodiment, the prostaglandin $I_2$ agonist is ((±)-(1R,2R,3aS,8bS)-2,3,3a,8b-tetrahydro-2-hydroxy-1-[(E)-(3S,4RS)-3-hydroxy-4-methyl-1-octen-6-ynyl]-1H-cyclopenta[b]benzofuran-5-butanoic acid or salt thereof.

In one embodiment, the internal regeneration factor production inducing agent is a sustained-release preparation of (E)-[5-[2-[1-phenyl-1-(3-pyridyl)methylideneaminoxy]ethyl]-7,8-dihydronaphthalen-1-yloxy]acetic acid.

In one embodiment, the internal regeneration factor production inducing agent is a microsphere (MS) preparation of (E)-[5-[2-[1-phenyl-1-(3-pyridyl)methylideneaminoxy]ethyl]-7,8-dihydronaphthalen-1-yloxy]acetic acid.

In one embodiment, the microsphere preparation is constituted by polylactic acid, polyglycolic acid, or poly(lactic-co-glycolic acid) or a mixture thereof or a hydrogel that is a biodegradable high-molecular weight compound.

In one embodiment, the biodegradable high-molecular weight compound is constituted by polylactic acid, polyglycolic acid, or poly(lactic-co-glycolic acid), having a weight average molecular weight of 5,000 to 50,000 or a mixture thereof, or a hydrogel.

In one embodiment, the microsphere preparation has a drug content from 15 to 20% and a mean particle size from 25 to 36 μm.

In one embodiment, the myocardial support device is constituted by at least one high-molecular weight compound selected from the group consisting of polyester, aromatic polyamide fiber, polyglycolic acid, polylactic acid, and polydioxanone.

In one embodiment, the myocardial support device is constituted by at least one high-molecular weight compound selected from the group consisting of polyester or polyglycolic acid.

In one embodiment, the advanced heart failure treatment material of the present invention comprises an internal regeneration factor production inducing agent constituted by a microsphere preparation of (E)-[5-[2-[1-phenyl-1-(3-pyridyl)methylideneaminoxy]ethyl]-7,8-dihydronaphthalen-1-yloxy]acetic acid, a sustained-release preparation holding agent constituted by fibrin, atelocollagen, or gelatin, and a myocardial support device constituted by a polyester surgical suture or a polyglycolic acid surgical suture.

In one embodiment, the advanced heart failure treatment material of the present invention comprises an atelocollagen sheet that is impregnated with a microsphere preparation of (E)-[5-[2-[1-phenyl-1-(3-pyridyl)methylideneaminoxy]ethyl]-7,8-dihydronaphthalen-1-yloxy]acetic acid or a gelatin sheet that is impregnated with the microsphere preparation, and a myocardial support device constituted by a polyester surgical suture or a polyglycolic acid surgical suture.

In one embodiment, the advanced heart failure treatment material of the present invention is constituted by spraying an atelocollagen aqueous solution containing a microsphere preparation of (E)-[5-[2-[1-phenyl-1-(3-pyridyl)methylideneaminoxy]ethyl]-7,8-dihydronaphthalen-1-yloxy]acetic acid, a gelatin aqueous solution containing the microsphere preparation, or a fibrin aqueous solution containing the microsphere preparation on the myocardial support device constituted by a polyester surgical suture or a polyglycolic acid surgical suture.

In one embodiment, the advanced heart failure treatment material of the present invention is used for treatment of dilated cardiomyopathy, severe ischemic cardiomyopathy, inflammatory cardiomyopathy, chronic rejection associated with a heart transplantation, congestive heart failure, right heart failure resulting from pulmonary hypertension and the like, or diastolic heart failure.

In one embodiment, the advanced heart failure treatment material of the present invention is used for being fitted externally onto a heart of a mammal.

In the present invention, as an internal regeneration factor production accelerating agent that contains one or more selected from the group consisting of compounds that increase cAMP; for example, a prostaglandin (PG) $I_2$ agonist, an $EP_2$ agonist, and an $EP_4$ agonist, or various PDE inhibitors, and the like, a hydrogel having a sheet form, a film form, a powder form, an ointment form, a paste form, or a sponge form that contains an MS sustained-release preparation of an OX derivative (for example, a compound 1 that will be described later) that is a $PGI_2$ agonist, additionally having a $TXA_2$ synthetase inhibitory activity was produced, and then an integrated myocardial regeneration device was produced by conjugating these hydrogel materials. Bioabsorbable hydrogel is produced by using bioabsorbable high-molecular weight compounds such as fibrin, gelatin, collagen, and hyaluronic acid that can be used in clinical application. These materials have high molding processing properties, can easily form crosslinks by chemical modification, and have been already used in clinical application as hemostatic agents and the like. Also, as a result of changing the properties of these hydrogel materials, a period of in vivo absorption can be changed, sustained-release of pharmaceutical agents becomes possible, and a period during which a hydrogel material is attached to the heart can be adjusted. For example, with respect to gelatin, crosslinking can be performed by heating (for example, 120-150° C.), ultraviolet irradiation, γ-ray irradiation, formaldehyde treatment, or the like, and a basic group or an acidic group is incorporated into a molecule so that the incorporated molecule can serve as a sustained-release preparation of protein, peptide, low molecular compound, or the like (WO 2004/082657, WO 2006/085653, and Japanese Laid-Open Patent Publication No. 2008-137975). Also, atelocollagen and the like generated by reducing the antigenicity of collagen can be used.

Because hydrogel materials have biocompatibility, the biocompatibility for a device material is not compromised, and thus the hydrogel materials can be used as sheets, films, sponges, powders, gels, and coating holding agents for various types of heart shape correction nets (myocardial regeneration devices), in which the MS sustained-release preparation of an OX derivative is incorporated.

For example, as a method for producing a gelatin sheet containing a compound 1 MS that will be described later, which is one example of internal regeneration factor production inducing agents, the film-form gelatin sheet containing the compound 1 MS can be produced from a gelatin aqueous solution containing the compound 1 MS, by a cast method. It should be noted that there is no limitation on the kind of sheet materials as long as they are degradable absorbable high-molecular materials, similarly to gelatin, and are able to be mixed with the compound 1 MS.

As a method for producing a two-layered sheet constituted by a gelatin sheet containing the compound 1 MS and a cross-linked gelatin sheet, for example, the two-layered sheet can be produced by adding a small amount of water to dissolve a part of the gelatin sheet containing the compound 1 MS and adhering the partially dissolved gelatin sheet to the cross-linked gelatin sheet. It should be noted that there is no limitation on the adhesion method as long as adhesion portions cannot be easily separated therefrom in the body, and one example thereof is suture fixation.

As a method for fixing the two-layered sheet constituted by the gelatin sheet containing the compound 1 MS and the cross-linked gelatin sheet to a myocardial jacket, for example, a surgical suture can be used to perform suture fixation. It should be noted that there is no limitation on the kind of surgical sutures that are to be used, similar to the surgical suture that was used at the time of producing the myocardial jacket.

Also, as the fixing method, the compound 1 MS may be suspended in a fibrinogen aqueous solution, and then admixed with Ca ions and liquid thrombin, and the obtained mixture may be also administered to affected site by spraying (Beriplast P Combi-Set; CSL Behring, Bolheal; Astellas Pharma Inc., and the like). Also, the compound 1 MS aqueous suspension may be absorbed by a sheet preparation (Spongel; Astellas Pharma Inc., Gelfoam, Gelfilm; Pfizer Inc., Surgicel; Johnson & Johnson, and the like), the obtained sheet preparation may be encased by fibrin glue (Beriplast P Combi-Set, Bolheal, and the like) or an atelocollagen seal (Integran; Koken Co., Ltd, TachoSil, TachoComb: CSL Behring, and the like).

As a method for producing a water poorly-soluble cross-linked gelatin sheet, for example, a film-like gelatin sheet can be produced from a gelatin aqueous solution by a cast method, and the obtained gelatin sheet can be subject to dehydrothermal crosslinking treatment under vacuum at approximately 110° C. to 150° C. for approximately 6 to 24 hours to produce the water poorly-soluble cross-linked gelatin sheet. It should be noted that conditions for the dehydrothermal crosslinking treatment may be changed depending on the thickness or shape of a gelatin sheet that is to be intended, and thus there is no particular limitation on the above-described treatment conditions as long as water poorly-soluble properties can be obtained during a desired given period of time.

As a sheet material, any material can be used as long as dehydrothermal crosslinking treatment can be performed thereon, and for example, a high-molecular material and the like such as gelatin, collagen, and hyaluronic acid are particularly preferable. Also, a cross-linking method is not limited to dehydrothermal crosslinking, and chemical cross-linking using crosslinking agents, a physical crosslinking method by radiation or the like may be used, and there is no particular limitation on the crosslinking method. Also, a non-crosslinked, normal degradable absorbable high-molecular material (for example, polylactic acid, polyglycolic acid, poly-$\epsilon$-caprolactone, or the like) may be used as long as it is not degraded or absorbed and can maintain the shape to some extent in the body for a predetermined period of time, and there is no particular limitation on the type of the material.

Through the studies of formulating the compound 1 into sustained-release preparations (MS), we have already found a poly (lactic-co-glycolic acid) (PGLA) microsphere preparation of the compound 1 (the compound 1 MS), which is included in a compound shown in a general formula (I) that will be described later which is one type of internal regeneration factor production inducing agents, as a preparation that can keep a high local concentration of the compound 1 in heart tissues (DDS) by attachment thereof to the heart about once a week to once every four weeks, and that shows kinetics in blood like intravenous infusion for a long period of time even though administered subcutaneously or intramuscularly (WO 2008/047863). For example, the MS preparation of the compound 1 produced using PLGA5020 or PLGA5050 (or 5-50) or a mixed preparation thereof is used to produce the MS preparation having sustained-release properties for about 1 to 4 weeks. It should be noted that PLGA5020 is a copolymer of 50 mol % lactic acid and 50 mol % glycolic acid, and represents a weight average molecular weight of 20,000, and PLGA5050 is a copolymer of 50 mol % lactic acid and 50 mol % glycolic acid, and represents a weight average molecular weight of 50,000.

As a result of further studies, we have succeeded in the production of a long-term sustained-release MS preparation of the compound 1 having a sustained-release period of about 4 weeks to 24 weeks by using various types of polylactic acid (PLA), polyglycolic acid (PGA), and poly (lactic-co-glycolic acid) (PLGA). Examples of PLGA to be used include PLA0005, PLA0010, PLA0020, PLA0050, PGA0005, PGA0010, PGA0020, PGA0050, PLGA7520, and PLGA7550 (Wako Pure Chemical Industries, Ltd./ Mitsui Chemicals, Inc. and the like). It should be noted that PLA0005 represents polylactic acid having a weight average molecular weight of 5,000; PLA0010 represents polylactic acid having a weight average molecular weight of 10,000; and PLA0050 represents polylactic acid having a weight average molecular weight of 50,000. Similarly, PGA0005 represents polyglycolic acid having a weight average molecular weight of 5,000; and PGA0050 represents polyglycolic acid having a weight average molecular weight of 50,000. Also, PLGA7520 is a copolymer of 75 mol % lactic acid and 25 mol % glycolic acid, and represents a weight average molecular weight of 20,000; and PLGA7550 is a copolymer of 75 mol % lactic acid and 25 mol % glycolic acid, and represents a weight average molecular weight of 50,000. One to three types of the compound 1 MS produced by these polymers may be mixed. For example, in the case where the compound 1 MS preparation has been produced by using PLA0020, the MS preparation having a sustained-release period of about 16 weeks is produced.

According to the present invention, a cell-free, cardiovascular/myocardial regenerative remedy that is an alternative to a heart transplantation, artificial hearts, and a cell transplantation remedy can be performed for the prevention and/or treatment of advanced heart failure associated with dilated cardiomyopathy, severe ischemic cardiomyopathy, or the like. Moreover, it is also useful for the prevention and/or treatment of chronic rejection associated with a heart transplantation, congestive cardiac failure, right heart failure resulting from pulmonary hypertension and the like, diastolic heart failure, and the like. In addition, according to the advanced heart failure treatment material of the present invention, the toxicity of the heart patch preparation and the myocardial support device that constitute the treatment material is significantly low, and is sufficiently safe for use in a medical device.

BRIEF DESCRIPTION OF DRAWINGS

FIG. 2(a) is a view showing the state in which a sheet that contains an internal regeneration factor production inducing agent is attached to the heart, FIG. 2(b) is a view showing the state in which the sheet described in FIG. 2(a) is covered by a protecting sheet, and FIG. 2(c) is a view showing the state in which the entire lower portion (a ventricle portion) of the heart is surrounded by the myocardial support device so as to further cover the protecting sheet described in FIG. 2(b).

FIG. 7(a) is a diagram of a heart model unique to the canine and human hearts that have been produced by stereolithography technology, FIG. 7(b) is a diagram of a film model that is constituted by a thin film that has been produced so as to be fitted onto the heart model, FIG. 7(c) is a diagram showing an example of a myocardial jacket that fits onto a shape unique to the canine heart that has been produced from the film model, and FIG. 7(d) is a diagram showing an example of a myocardial jacket that fits onto the shape unique to the human heart that has been produced from the film model.

MODE FOR CARRYING OUT THE INVENTION

1. Advanced Heart Failure Treatment Material

Figure 1:
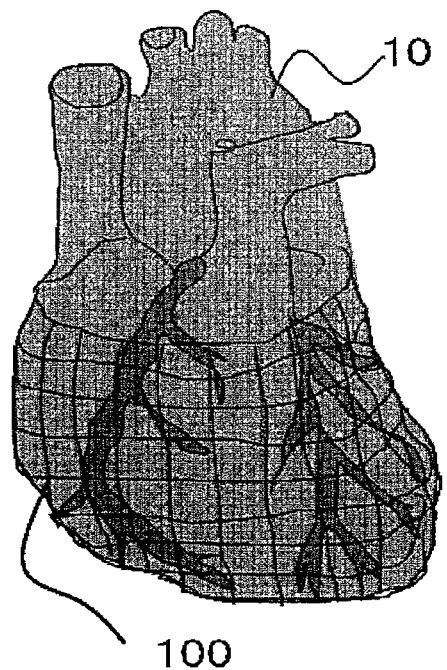
FIG. 1 is schematic view of an exemplary myocardial support device that constitutes an advanced heart failure treatment material of the present invention and is a view for illustrating the state in which the device is fitted onto the heart.

First, an advanced heart failure treatment material of the present invention will be described in detail.

The advanced heart failure treatment material of the present invention includes a pharmaceutical agent, an agent holding for the pharmaceutical agent, and a myocardial support device.

In one embodiment, the advanced heart failure treatment material of the present invention includes an internal regeneration factor production inducing agent, which is a sustained-release preparation, a bioabsorbable high-molecular weight compound, which is a sustained-release preparation holding agent, and a myocardial support device.

In another embodiment, the advanced heart failure treatment material of the present invention is configured by combining a sustained-release preparation of various types of internal regeneration factor production inducing agents, a sheet or spray in which bioabsorbable high-molecular weight compound that is a sustained-release preparation holding agent is used, and a myocardial support device.

In yet another embodiment, the advanced heart failure treatment material of the present invention is an integrated myocardial support device produced by coating a myocardial support device with sustained-release preparation of various types of internal regeneration factor production inducing agents using a bioabsorbable high-molecular weight compound, which is a sustained-release preparation holding agent.

In the present invention, a term "pharmaceutical agent" includes a pharmaceutical material that is systemically or topically administered in an oral or parenteral form, but is not particularly limited thereto as long as it is being used for heart failure treatment. Specific examples of a pharmaceutical agent include proteins such as internal regeneration factor proteins, and polypeptides; genes such as internal regeneration factor production genes, polynucleotides, and antisenses; compounds such as internal regeneration factor production inducing agents, and low molecular compounds; cells such as stem cells, iPS cells, and somatic cells isolated from tissues; decoys; antibodies; extracellular matrixes; cell adhesion factors; and vaccines. Examples of the low molecular compounds include antithrombotic agents, circulation-improving agents, smooth muscle extension agents, anti-inflammatory agents, local anesthetics, analgesic agents, metabolism improving agents, and prostaglandins. As a "pharmaceutical agent" in the present invention, one type of these pharmaceutical materials may be used, or a plurality types thereof may be combined. In one embodiment, the "pharmaceutical agent" is an internal regeneration factor production inducing agent. Moreover, it is preferable that the internal regeneration factor production inducing agent is a sustained-release preparation.

1.1 Internal Regeneration Factor Production Inducing Agent (Sustained-Release Preparation)

In the present specification, examples of internal regeneration factors include vascular endothelial growth factor (VEGF), hepatocyte growth factor (HGF), various types of fibroblast growth factor (a/b-FGF), transforming growth factor-β (TGF-β), platelet-derived growth factor (PDGF), angiopoietin, hypoxia inducible factor (HIF), insulin-like growth factor (IGF), bone morphogenetic protein (BMP), connective tissue growth factor (CTGF), epidermal growth factor (EGF), nerve growth factor (NGF), brain-derived neurotrophic factor (BDNF), glial cell-derived neurotrophic factor (GDNF), stem cell factor (SCF), stromal cell-derived factor (SDF-1), granulocyte colony-stimulating factor (G-CSF), keratinocyte growth factor (KGF), chondrocyte growth factor (GDF), leukocyte proliferation inhibitory factor (LIF), and Kruppel-like transcription factor (KLF), or growth factors of the families. Also, examples of internal regeneration factors include extracellular matrixes (for example, fibronectins, laminins, and proteoglycans), and cell adhesion factors (for example, cadherins, and integrins).

The internal regeneration factor production inducing agent is a pharmaceutical agent that contains one or more selected from for example, a $PGI_2$ agonist, an $EP_2$ agonist, and an $EP_4$ agonist. Moreover, examples of the internal regeneration factor production inducing agents include an AT1 receptor blocker (ARB), a peroxisome proliferator-activated receptor-γ (PPARγ) agonist, a phosphodiesterase (PDE) inhibitor, IL-1, TNF-α, and INF, in addition to Cholera toxin, 8-bromo-cAMP, dibutyl-cAMP, and forskolin.

For example, examples of the prostaglandin (PG) $I_2$ agonist that is the internal regeneration factor production inducing agent include compound represented by a general formula (I) and a salt thereof:

[Formula 3]

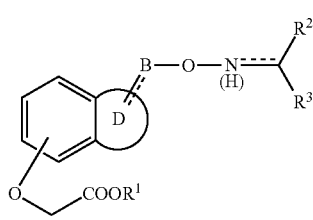

(in the formula,

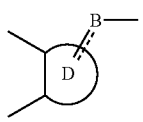

is

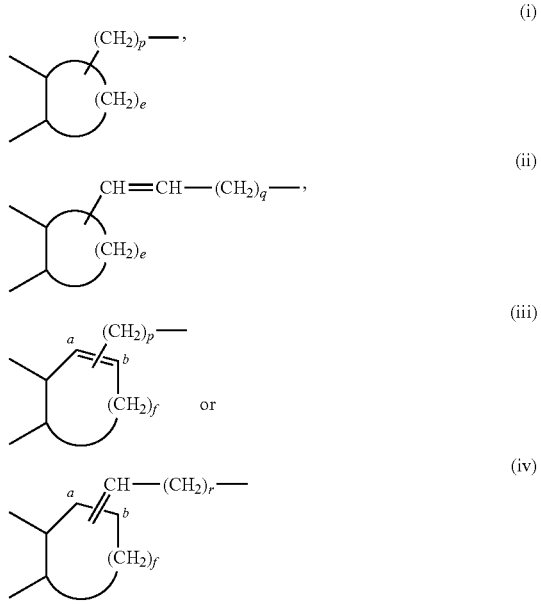

(wherein,
$R^1$ represents a hydrogen atom or a C1-4 alkyl group,
$R^2$ represents (i) a hydrogen atom, (ii) a C1-8 alkyl group, (iii) a phenyl group or a C4-7 cycloalkyl group, (iv) a 4-7-membered single ring containing one nitrogen atom, (v) a C1-4 alkyl group substituted by a benzene ring or a C4-7 cycloalkyl group, or (vi) a C1-4 alkyl group substituted by 4-7-membered single ring containing one nitrogen atom,
$R^3$ represents (i) a C1-8 alkyl group, (ii) a phenyl group or a C4-7 cycloalkyl group, (iii) a 4-7-membered single ring containing one nitrogen atom, (iv) a C1-4 alkyl group substituted by a benzene ring or a C4-7 cycloalkyl group, or (v) a C1-4 alkyl group substituted by a 4-7-membered single ring containing one nitrogen atom,
e represents an integer of 3 to 5, f represents an integer of 1 to 3, p represents an integer of 1 to 4, q represents 1 or 2, and r represents an integer of 1 to 3, provided that in the case where

[Formula 4]

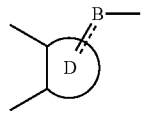

is the group indicated by the above (iii) or (iv), —$(CH_2)_p$— and =CH—$(CH_2)_r$— are bound to a or b on the ring, and a ring in $R^2$ and $R^3$ may be substituted by one to three C1-4 alkyl groups, C1-4 alkoxy groups, halogen atoms, nitro groups, or trihalomethyl groups).

In the compound represented by the general formula (I) or a salt thereof, it is preferable that $R^2$ is (iii) a phenyl group or a C4-7 cycloalkyl group, (iv) a 4-7-membered single ring containing one nitrogen atom, (v) a C1-4 alkyl group substituted by a benzene ring or a C4-7 cycloalkyl group, or (vi) a C1-4 alkyl group substituted by a 4-7-membered single ring containing one nitrogen atom, and it is particularly preferable that $R^2$ is (iii) a phenyl group or a C4-7 cycloalkyl group, or (iv) a 4-7-membered single ring containing one nitrogen atom.

In the compound represented by the general formula (I) or a salt thereof, it is preferable that $R^3$ is (ii) a phenyl group or a C4-7 cycloalkyl group, (iii) a 4-7-membered single ring containing one nitrogen atom, (iv) a C1-4 alkyl group substituted by a benzene ring or a C4-7 cycloalkyl group, or (v) a C1-4 alkyl group substituted by a 4-7-membered single ring containing one nitrogen atom, and it is particularly preferable that $R^3$ is (ii) a phenyl group or a C4-7 cycloalkyl group, or (iii) a 4-7-membered single ring containing one nitrogen atom.

Furthermore, among compound represented by the general formula (I) or a salt thereof, oxime derivatives, namely, (E)-[5-[2-[1-phenyl-1-(3-pyridyl)methylideneaminoxy]ethyl]-7,8-dihydronaphthalen-1-yloxy]acetic acid (the compound 1):

[Formula 5]

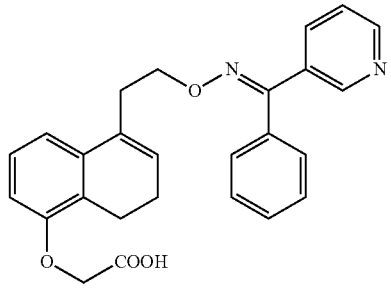

and (Z)-[5-[2-[1-phenyl-1-(3-pyridyl)methylideneaminoxy]ethyl]-7,8-dihydronaphthalen-1-yloxy]acetic acid (compound 2):

[Formula 6]

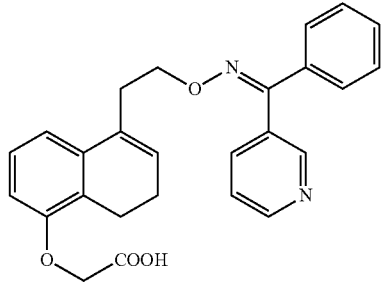

are more preferable.

Also, examples of other $PGI_2$ agonists include beraprost sodium: ((±)-(1R,2R,3aS,8bS)-2,3,3a,8b-tetrahydro-2-hydroxy-1[(E)-(3S,4RS)-3-hydroxy-4-methyl-1-octene-6-ynyl]-1H-cyclopenta[b]benzofuran-5-butanoic acid sodium salt) (compound 3); OP-2507: (5-{(3aR,4R,6aS)-5-hydroxy-4-[(1E,3S)-3-hydroxy-3-(cis-4-propyl cyclohexyl)prop-1-enyl]-3,3a,4,5,6,6a-hexahydrocyclopenta[b]pyrrole-2-yl}pentanoic acid methyl ester (compound 4); NS-304 ($PGI_2$ agonist made by Nippon Shinyaku Co., Ltd.); MRE-269 ($PGI_2$ agonist made by Nippon Shinyaku Co., Ltd.); and various types of carbacyclin derivatives, but the above-described compound 1 or compound 3 is preferable which is chemically stable.

U.S. Pat. No. 5,480,998 discloses that because the above-described compound 1 or a non-toxic salt thereof, an oxime (OX) derivative of the general formula (I) and used in the present invention as a $PGI_2$ agonist has platelet aggregation inhibitory action, platelet adhesion inhibitory action, vasodilator action, and gastric acid secretion inhibitory action, such oxime is useful for the prevention and/or treatment of thrombosis, arteriosclerosis, ischemic heart diseases, gastric ulcer, hypertension, and the like. Also, WO 2004/032965 and WO 2008/047863 disclose that such oxime is useful for various types of cellular/organ dysfunction due to angiogenic activities, differentiation-inducing action of various types of stem cells, anti-apoptotic action, anti-fibrosis action, and the like based on internal regeneration factor production promoting action.

Prostaglandins (PGs), which are classified into autacoids, can be biosynthesized in a required amount when needed at a site where it is required, and rapidly metabolized and inactivated locally after onset of action. Therefore, unlikely hormones, PGs do not circulate systemically. There has been a problem in that PGs have a short half-life in blood due to chemical instability in clinical application, and exhibit hypotensive action, headache, flushing, and the like associated with vasodilator action when used as injection in systemic administration, and diarrhea induction action, intussusception, and the like in addition to hypotensive action when used as an oral preparation. We have studied possibility of direct administration of a sustained preparation to an affected local site in order to avoid these problems.

We considered that if the compound such as indicated by the above-described general formula (I) or the above-described compound 1 could be sustainedly released to an ischemia site where angiogenesis was required or an injured local site where tissue repair was required, it would become possible to sustainedly induce production of various types of internal regeneration factors in the vicinity of the injured local site, in addition to vasodilator action of residual blood vessels in the ischemia region and blood flow rate increasing action in platelet aggregation inhibitory action, so as to create a DDS (drug delivery system) preparation that has reduced side effects compared with systemic administration. Moreover, we considered that if such compounds could be formulated into preparations capable of being sustainedly released over a period during which angiogenesis (regeneration) and tissue repair occurred in the ischemia site or in the vicinity of the local site of injured tissues, it would allow for creating pharmaceutical agents such that side effects could be reduced in systemic administration and dosing frequency could be reduced to improve administration compliance.

Sustained-release preparations of various types of internal regeneration factor production inducing agents and methods for producing them have well been known, and the details thereof are disclosed in, for example, WO 2004/032965 and WO 2008/047863.

That is to say, it is sufficient that the sustained preparations can able to sustainedly supply active substances to a region of a disease, and there is no limitation thereto. Examples thereof include sustained-release injections (for example, a microcapsule preparation, a microsphere preparation, a nanosphere preparation, and the like), an embedded preparation (for example, a film preparation, and the like), ointment, a coating preparation whose effective substances are contained in or that coats a medical appliance (a stent, a fixing bolt, a surgical suture, or the like), and the like.

The microcapsule preparation, microsphere preparation, and nanosphere preparation in the present invention are pharmaceutical compositions that contain an effective substance as an active ingredient and have a fine particle-like form with biodegradable polymer.

A drug sustained-release system of the present invention involves bioabsorbable high-molecular weight compounds, and is achieved by natural high-molecular weight compounds, or synthetic high-molecular weight compounds. A mechanism for controlling a sustained-release rate therefrom includes a controlled-degradation model, a controlled-diffusion model, a controlled-membrane permeation model, and the like.

Examples of a natural high-molecular weight compound that is a bioabsorbable high-molecular weight compound of the present invention include plant-produced polysaccharides (for example, cellulose, starch, alginic acid, and the like), animal-produced polysaccharides and proteins (for example, chitin, chitosan, collagen, gelatin, albumin, glycosaminoglycans, and the like), microorganism-produced polyesters and polysaccharides (for example, poly-3-hydroxyalkanoate hyaluronic acid, and the like).

Also, examples of a biodegradable polymer include fatty acid polyester or a copolymer thereof, polyacrylic acid esters, polyhydroxy butyric acids, polyalkylene oxalates, polyorthoester, polycarbonate, and polyamino acids, and these can be used alone or in combination. Examples of fatty acid polyester or a copolymer thereof include polylactic acid, polyglycolic acid, polycitric acid, polymalic acid, polyethylene succinate, polybutylene succinate, poly-$\epsilon$-caprolactone, polybutylene terephthalate-adipate or poly(lactic-co-glycolic acid), and these can be used alone or in combination. In addition, poly-$\alpha$-cyanoacrylic acid ester, poly-$\beta$-hydroxybutyric acid, polytrimethyleneoxate, polyorthoester, polyorthocarbonate, polyethylene carbonate, poly-$\gamma$-benzyl-L-glutamic acid, polyvinyl alcohol, polyester carbonate, polyanhydride, polycyanoacrylate, polyphosphazene or poly-L-alanine can be used alone or in combination. Polylactic acid, polyglycolic acid, or poly(lactic-co-glycolic acid) is preferable, and poly(lactic-co-glycolic acid) is more preferable.

The average molecular weight of these biodegradable polymers that are used in the present invention is preferably approximately 2,000 to approximately 800,000, and more preferably approximately 5,000 to approximately 200,000. For example, polylactic acid preferably has a weight average molecular weight of approximately 5,000 to 100,000, and more preferably approximately 6,000 to approximately 50,000. Polylactic acid can be synthesized in accordance with a known production method. Poly(lactic-co-glycolic acid) preferably has a composition ratio of lactic acid and glycolic acid of approximately 100/0 to approximately 50/50 (W/W), and particularly preferably approximately 90/10 to 50/50 (W/W). Poly(lactic-co-glycolic acid) preferably has a weight average molecular weight of approximately 5,000 to approximately 100,000, and more preferably approximately 10,000 to 80,000. Poly(lactic-co-glycolic acid) can be synthesized in accordance with a known production method. Also, basic amino acids (for example, alginic acid) and the like may be added thereto in order to suppress initial burst.

In the present specification, weight average molecular weight refers to molecular weight in terms of polystyrene measured by gel permeation chromatography (GPC).

The above-described biodegradable polymer can be modified depending on the strength of pharmacological activity of effective substances and drug release of interest as long as the object of the present invention is achieved, and for example, the biodegradable polymer is used in an amount of approximately 0.2 to 10,000 times (mass ratio) with respect to the biologically active substance, preferably in an amount of approximately 1 to 1,000 times (mass ratio), and more preferably in an amount of approximately 1 to 100 times (mass ratio).

Microspheres, microcapsules, and nanocapsules of the present invention are produced by, for example, underwater drying (for example, an o/w method, a w/o method, a w/o/w method, and the like), a phase separation method, spray drying, a granulation method using supercritical fluid, a method equivalent thereto, or the like.

Specifically, as a result of various studies, we have newly found to produce a microsphere (MS) preparation with poly(lactic-co-glycolic acid) (PLGA) (the compound 1 MS) based on structural features of the above-described compound 1. The preparation is designed such that the compound 1 MS can be hydrolyzed to lactic acid and glycolic acid at an administered site, and the contained compound 1 can be approximately linearly released therefrom to the living body. Currently, preparations having a sustained-release period of 1 week to 4 weeks have been found by changing the molecular weight of PLGA, lactic acid/glycolic acid ratio, a particle size, and the like (WO 2008/047863).

Also, similarly, the compound 1 MS can be used as the preparation like intravenous infusion for a long period by subcutaneous administration or intramuscular injection.

Although myocardial stem cells that can divide and differentiate into myocardial cells have been found in the heart due to advances in the recent tissue stem cell research (Beltrami A P, et al., Cell 19:763-776, 2003, Oh H, et al., Proc. Natl. Acad. Sci. USA, 100:12313-12318, 2003, Laugwitz K L, et al., Nature, 433(7026):647-653, 2005, Smart N, et al., Nature, 2011, Jun. 8; 474(7353)), there has been currently no treatment material that can guide myocardial stem cells to a lesion, and controls proliferation and differentiation so as to regenerate myocardia by the function of the material itself.

The compound 1 is a low molecular OX derivative having the non-PG skeleton, and $TXA_2$ synthase inhibitory action as well as selective IP agonist action is integrated into the molecule. As a result of the studies of pharmacologic actions including these features of the compound 1, the compound 1 indicates various types of internal regeneration factors such as hepatocyte growth factor (HGF), vascular endothelial growth factor (VEGF), epidermal growth factor (EGF), insulin-like growth factor (IGF-1), stromal cell-derived factor (SDF-1), and granulocyte colony-stimulating factor (G-CSF) under coculture of NHDF and HUVEC.

Because the production of various types of these internal regeneration factors is induced, anti-apoptotic action, angiogenesis promoting action, stem cell differentiation-inducing action, anti-fibrosis action, and the like can be expected.

Also, we have found that the compound 1 suppresses phosphorylation of ERK1/2 that has progressed due to pathology by activation of cAMP/PKA, and also suppresses migration, proliferation, and collagen production of fibroblasts (Am. J. Respir. Crit. Care. Med., 177, 195-201 (2008)).

Meanwhile, it was shown that the compound 1 suppresses the increases in ALT and AST in blood, and exhibits hepatocyte protection effects due to anti-apoptotic action and anti-necrosis action in acute hepatopathy induced by carbon tetrachloride. Also, these protection effects are reduced by administration of anti-HGF neutralizing antibody (Am. J. Physiol. Gastrointest Liver Physiol., 302: G420-G429, 2012). Various types of pharmacologic actions and the like of the compound 1 are described in literature (for example, The Cell, 43(10); 26-35(2011), and The Cell, 44(2)34-40 (2012)).

We have confirmed the effectiveness regarding the effects of the compound 1 on advanced heart failure by administrating the compound 1 MS to myocardia in ischemic heart failure models of mice (Clin. Sci., 112, 607-616 (2007)) and pigs (Life Science, 85: 255-261 (2009)). Also, we have confirmed the effectiveness by administrating the compound 1 MS to myocardial, similarly using canine high speed paging (dilated cardiomyopathy) model (ATS2011; international conference/American Thoracic Society/Colorado Denver (2011), AHA2011; American Heart Association Orlando Fla. USA (2011)). However, these direct administrations of the pharmaceutical agent to myocardia could not exhibit stable pharmacological effect in a wide range, and arrhythmia frequently occurred, and thus it seemed that the success of clinical application was hard.

On the other hand, the inventors have confirmed the effectiveness by intermittent subcutaneous administration of the compound 1 MS in rat ischemic heart failure model (Biomedicine & Aging Pathology, 1; 90-96 (2011), European Journal of Pharmacology, 2012, 674 352-358), hamster dilated cardiomyopathy model (Biomedicine & Pharmacotherapy, 2009, 63: 781-786), pulmonary hypertension model (Am. J. Respir. Crit. Care Med., 177, 195-201 (2008)) and mouse cardiac transplantation chronic rejection model (International Heart Journal, 53:64-67(2012)), but it seemed that because of systemic administration, the deviation of systemic side effects (hypotensive action, platelet aggregation inhibitory action, and the like) and the effectiveness is small. Meanwhile, patches having an aim of persistence in a disease local site are also studied. For example, the inventors have studied the effectiveness of attaching a self-myoblast sheet to the heart, in a case of advanced heart failure. It has been suggested that these cell sheet therapies (SMBCT) improve cardiac functions by internal regeneration factors such as HGF that are sustainedly produced from cells (J. Thoracic and Cardiovascular Surgery, 2006; 132, 918-924).

Also, the inventors have confirmed the effectiveness by administration via direct attachment of a sheet having the compound 1 MS impregnated with an atelocollagen membrane to the heart of a spontaneous dilated cardiomyopathy hamster model.

Moreover, the inventors have confirmed that as a result of attaching the compound 1 MS to the heart in the same model, the concentration of the compound 1 in the heart tissues was higher than the concentration thereof in blood by about 10 to 300 times and the effectiveness sustained for a long period of time (AHA2011; American Heart Association Orlando Fla. USA (2011)).

Based on these results, the inventors found that sheets containing the compound 1 MS could sustainedly keep a local concentration of the drug at a high concentration in an attached organ part (DDS), and could keep stable pharmacologic actions with reduced onset of side effects, but the effects were not sufficient to be an alternative to artificial hearts or a heart transplantation therapy.

Meanwhile, the present organ/tissue patch therapy can be applied to not only heart diseases but also kidney diseases, pulmonary diseases, liver diseases, bone disease, skin disease, and the like of other organs, using a DDS patch.

In one embodiment of the present invention, the sustained-release preparation of the above-described internal regeneration factor production inducing agent is contained in a form of a sheet or spray along with the other components (for example, gelatin, fibrin, collagen, and hyaluronic acids). There is no particular limitation on content of the internal regeneration factor production inducing agent and the other components in the sheet or spray, and the content thereof is arbitrarily set by a person skilled in the art.

It should be noted that, for example, U.S. Pat. No. 5,480,998 discloses a method for producing, for example, compounds indicated by the general formula (I) (for example, including (E)-[5-[2-[1-phenyl-1-(3-pyridyl)methylideneaminoxy]ethyl]-7,8-dihydronaphthalen-1-yloxy]acetic acid (the compound 1), among the above-described $PGI_2$ agonists that can be used in the present invention. Also, for example, WO 1996/026721 discloses a method for producing beraprost sodium: ((±)-(1R,2R,3aS,8bS)-2,3,3a,8b-tetrahydro-2-hydroxy-1[(E)-(3S,4RS)-3-hydro xy-4-methyl-1-octene-6-ynyl]-1H-cyclopenta[b]benzofuran-5-butanoic acid sodium salt). Also, methods for producing sustained-release preparations containing these compounds are disclosed in, for example, WO 2004/032965 and WO 2008/047863.

1.2 Agent Holding for the Pharmaceutical Agent (Sustained-Release Preparation Holding Agent)

In the advanced heart failure treatment material of the present invention, an agent holding for the pharmaceutical agent plays an important role for fixing a pharmaceutical agent to myocardia or a myocardial support device and sustainedly causing drug efficacy to be exerted as well as exerting synergistic effects on advanced heart failure together with the effects of the myocardial support device.

The agent holding for the pharmaceutical agent of the present invention is constituted by a bioabsorbable high-molecular weight compound or a biodegradable polymer.

Examples of a natural high-molecular weight compound that is bioabsorbable high-molecular weight compound used as an agent holding for the pharmaceutical agent include plant-produced polysaccharides (for example, cellulose, starch, alginic acid, and the like), animal-produced polysaccharides and proteins (for example, chitin, chitosan, collagen, gelatin, albumin, glycosaminoglycan, and the like), microorganism-produced polyesters and polysaccharides (for example, poly-3-hydroxyalkanoate, hyaluronic acid, and the like). Fibrin, gelatin, collagen, and hyaluronic acid are preferable, and fibrin, atelocollagen, and gelatin are more preferable.

Examples of a biodegradable polymer that is used as the agent holding for the pharmaceutical agent include fatty acid polyester or a copolymer thereof, polyacrylic acid esters, polyhydroxy butyrates, polyalkylene oxalates, polyorthoester, polycarbonate, and polyamino acids, and these can be used alone or in combination. Examples of fatty acid polyester or copolymer thereof include polylactic acid, polyglycolic acid, polycitric acid, polymalic acid, polyethylene succinate, polybutylene succinate, poly-ϵ-caprolactone, polybutylene terephthalate-adipate, and poly(lactic-co-glycolic acid), and these can be used alone or in combination. In addition, poly-α-cyanoacrylate, poly-β-hydroxybutyrate, polytrimethyleneoxate, polyorthoester, polyorthocarbonate, polyethylene carbonate, poly-γ-benzyl-L-glutamic acid, polyvinyl alcohol, polyester carbonate, polyanhydride, polycyanoacrylate, polyphosphazene or poly-L-alanine can be used alone or in combination. Polylactic acid, polyglycolic acid, or poly(lactic-co-glycolic acid) is preferable, and poly(lactic-co-glycolic acid) is more preferable.

It is possible to add an additive agent that will be described later to the agent holding for the pharmaceutical agent of the present invention.

The agent holding for the pharmaceutical agent of the present invention can be used in a form of a sheet that is impregnated with a pharmaceutical agent or a spray that contains a pharmaceutical agent. The sheet and spray can be produced by a known method that will be described later.

1.3 Myocardial Support Device

In the advanced heart failure treatment material of the present invention, a myocardial support device may be a conventionally known device. A method for producing a myocardial support device is disclosed in, for example, WO 2000/002500, WO 2001/095832, and Japanese Patent No. 4582549.

Conventionally, a heart shape correction net (a jacket) that is to be fitted onto the outer side of the heart has been proposed as one of medical appliances for heart disease treatment (for example, WO 2001/085061, and U.S. Pat. No. 5,702,343.) The above-described medical appliance is made by forming cloth having a mesh structure into a cup shape, and is for preventing heart from dilating and preventing aggravation of heart failure by being fitted onto the outer side of the dilated heart of a heart failure patient.

It has been suggested that such a conventional net serves as a heart shape correction net that is useful in restricting excessive dilation of the heart by accommodating a portion of the heart, and surrounding the accommodated portion from outside (for example, WO 2000/002500 and Japanese Patent No. 4582549).

Here, it is conceivable that ventricle remodeling promotes heart failure as a result of heart dilation not only increasing myocardial tension and oxygen consumption but also inducing various types of stress reaction. The heart shape correction net suppresses ventricle remodeling, and is a method for mechanically (forcibly) suppressing heart dilation.

In this manner, a mesh-like myocardial support device to which Laplace's principle is applied suppresses myocardial remodeling and cardiomegaly, and improves the shape and function of the dilated heart so as to suppress or maintain progress of heart failure. However, although such a myocardial device has been already developed by ACORN CARDIOVASCULAR Inc. in U.S.A. as CorCap™, results of clinical trials have been insufficient, and thus development has been stopped.

Currently, an improved heart shape correction net that is to be in closer contact with the heart has been developed, and can not only prevent the dilation of heart but also deal with associated mitral insufficiency due to a complication (Japanese Patent No. 4582549).

With respect to such a conventional heart shape correction net, a myocardial support device in advanced heart failure treatment material of the present invention is constituted by a material and in a form that will be described below, for example.

The myocardial support device is constituted by an elastic material such as a net, a knitted item, and a textile. For example, in the case where the myocardial support device is a net, yarn used for a net is made of a biocompatible material, and there is no particular limitation on the quality and the width of the material as long as it has appropriate ability to be used as the conventional heart shape correction net. Examples of yarn include twisted monofilaments such as polyester, polytetrafluoroethylene, foamed polytetrafluoroethylene (foamed PTFE, ePTFE), polypropylene, and poly-2-fluorinated ethylene (hexafluoropropylene-vinylidene fluoride).

The yarn made of these materials may be formed by using any one type of the above-described biocompatible materials, or two or more types thereof. Alternatively, the yarn may be a conjugated fiber material in which fiber having more strength (for example, aromatic polyamide fiber) is used as a core material in order to increase fatigue resistance and disconnection resistance.

Alternatively, a net may be produced by using the yarn made of these materials that is fiber of a biodegradable material (PGA, PLA, PLGA, polydioxanone (PDS), caprolactone, silk fibroin, cellulose, chitin, chitosan, keratin, polyvinyl alcohol, and the like). It is preferable that a material of fiber has a density of 70 dtex or greater.

There is no particular limitation on a knitting form in the myocardial support device, and for example, Jersey stitch and mesh stitch can be adopted.

In the present invention, for example, as shown in FIG. 1, a myocardial support device 100 has a bag-like shape that can surround, in particular, a lower portion, in other words, a ventricle portion, of a heart 10. Alternatively, the myocardial support device 100 may have a cylindrical shape having opened top and bottom. There is no particular limitation on the size of the myocardial support device, and for example, the device is designed so as to surround the exaggerated human heart (for example, taking individual differences, such as adult, male, female, and child, into consideration), and to have a size according to which the device can stretch in accordance with beats of the heart.

WO 2000/002500 and Japanese Patent No. 4582549 disclose that in the present invention, a mesh-like myocardial support device to which Laplace's principle is applied suppresses myocardial remodeling and cardiomegaly, and improves the shape and function of the dilated heart so as to suppress or maintain progress of heart failure.

In order to produce a myocardial support device (a myocardial jacket) that fits the specific shape of a canine or human heart having a complex three dimensional shape, it is necessary to produce a pattern having the specific shape of a canine or human heart. As a method for producing a pattern having the specific shape of a canine or human heart, for example, a heart model having such a specific shape is produced by stereo lithography using three dimensional data on a canine or human heart obtained by diagnostic imaging technology (MRI, CT scan, or the like), and a thin film layer is produced so as to have a shape that exactly fits the heart model. Thereafter, the obtained film is cut and unfolded so as to obtain a pattern that fits the unique canine or human heart.

Alternatively, based on three dimensional data obtained by diagnostic imaging technology, for example, three dimensional data can be directly divided in and expanded to two dimensional data using commercial software such as DressingSimEX or LookStailor. Also, it is possible to create pattern data based on the two dimensional expanded data. In other words, it is possible to obtain pattern data on the specific shape of a canine or human heart directly from digital data without actually producing a model or a structure. It should be noted that there is no particular limitation on software used in data processing as long as it has a function for expanding three dimensional data to two dimensional data.

As a method for producing the myocardial jacket from pattern data on the specific shape of a canine or human heart, for example, a myocardial jacket that fits the specific shape of a canine or human heart can be produced using a surgical suture by a three-dimensional seamless wholegarment knitting machine (SWG041 model) made by SHIMA SEIKI MFG., LTD. It should be noted that there is no particular limitation on the quality (polyester, silk, polypropylene filature, and the like), the property (monofilament, multifilament, braid, and the like), degradability, and the like of the material of the surgical suture to be used, as long as it is able to construct the shape of the myocardial jacket.

For example, as a method for sustainedly releasing an internal regeneration factor derivative like the above-described compound 1 for a long-term from the myocardial jacket, a two-layered sheet constituted by a gelatin sheet containing the above-described compound 1 MS and a water poorly-soluble cross-linked gelatin sheet is fixed to the inner face of the myocardial jacket such that the cross-linked gelatin sheet comes into contact with the myocardial jacket, and thereby the gelatin sheet containing the compound 1 MS on the myocardial side is not degraded or absorbed immediately in the body due to a barrier of the cross-linked gelatin sheet and can sustainedly release compound 1 to myocardia for a long-term.

In view of this, as a result of the earnest research, the present inventors have newly found that, as will be described later, a myocardial support device to which Laplace's principle is applied is combined with a sheet or spray of an MS agent of the OX derivative compound 1, and the like which induces various types of internal regeneration factors, onto the heart, and thereby, compared with each drug alone, extremely significant high effectiveness can be achieved due to synergistic effects of actions, with respect to advanced heart failure.

Also, by coating the sustained-release MS preparation of the OX derivative (the compound 1) to the myocardial support device using bioabsorbable high-molecular weight compound, an integrated cardiovascular/myocardial regeneration device that can be clinically used for general use has been successfully produced.

Moreover, as a result of the earnest research, we have newly found that as a result of newly using a mesh-like myocardial support device to which Laplace's principle is applied with the internal regeneration factor production inducing agent such as compound 1, of an OX derivative, for example, by combining with a regeneration therapy using a sheet of the sustained-release MS preparation of the compound 1, a derivative thereof, regeneration of cardiac blood vessels and myocardia is promoted, heart failure is cured, and the recurrence is suppressed due to the OX derivative, in addition to the shape and function of the dilated heart being improved, and myocardial remodeling and cardiomegaly being suppressed, and progress of heart failure being suppressed.

It should be noted that, for example, an apparatus and a method for localizing a therapeutic agent to a heart shape correction net (a jacket) so as to deliver the drug to a target region of the heart and/or peripheral tissues is described in WO 2001/095832.

However, the compound indicated by the general formula (I) or the compound 1 MS is not specifically disclosed as the therapeutic agent. Meanwhile, as described above, it has been known that stable pharmacologic actions with reduced onset of side effects can be sustained by directly attaching a sheet containing the compound 1 MS to the heart. However, the effects of any methods described above were not sufficient to be an alternative to artificial hearts or a heart transplantation therapy.

In other words, in an advanced heart failure treatment material of the present invention, a myocardial support device to be used is not only used to exert only a function as a heart shape correction net such as described in WO 2001/095832, but also achieves arrangement of a pharmaceutical agent and an agent holding for the pharmaceutical agent to a desired position of the heart using appropriate elasticity and flexibility of the device. This arrangement does not particularly require attachment of a biocompatible adhesive or attachment component, and thus the device is particularly useful in that the device can be quickly fitted in risky area limited time during dangerous cardiac surgery.

We have found that the present invention involves two therapies having completely different anti-heart failure action mechanisms, that is, combines a myocardial support device to which Laplace's principle is applied and an OX derivative compound 1 MS, and the like that induces various types of internal regeneration factors so as to achieve extremely significant high effectiveness due to synergistic effects of the actions, compared with each single-drug, and that the present invention is a treatment method that can be an alternative to conventional artificial hearts and heart transplantation therapy.

Also, the myocardial support device was coated by internal regeneration factor production inducing agent derivative such as the sustained-release MS preparation of an OX derivative (for example, the compound 1) using a bioabsorbable high-molecular material (gelatin, fibrin, collagen, and hyaluronic acid and the like), and thereby an advanced heart failure treatment material for an integrated cardiovascular/myocardial regeneration device that can be clinically used for general use has been successfully produced.

2. Application as a Medical Device

The combination of the myocardial support device and the sustained-release preparation or the integrated myocardial support device, of the present invention is adapted to advanced heart failure as a result of heart disease (for example, myocardial infarction, angina pectoris, supraventricular tachyarrhythmia, congestive heart failure, diastolic heart failure, idiopathic cardiomyopathy, dilated cardiomyopathy, atrial fibrillation, myocarditis, heart transplantation chronic rejection, and the like).

Meanwhile, the sustained-release preparation in which an internal regeneration factor production accelerating agent having cAMP production accelerating action is used is directly attached to various disease organs (parts) in the form of sheet, spray, ointment, or the like using a bioabsorbable high-molecular weight compound, as a result of which stable usefulness is achieved for a long period of time. Because the $PGI_2$ agonist has internal regeneration factor production accelerating action, due to angiogenesis accelerating action and differentiation-inducing action from various stem cells for tissue repair, the $PGI_2$ agonist is useful as preventive and/or therapeutic agents for various types of organ dysfunction, for example, liver diseases (for example, fulminant hepatitis, acute hepatitis, chronic hepatitis, cirrhosis, fatty liver, liver transplantation, and the like), kidney diseases (for example, acute kidney injury (AKI), chronic kidney disease (CKD), glomerulonephritis, nephrosclerosis, renal dysfunction of dialysis patients, ischemic renal dysfunction, renal tubular transport disorders, Cushing's syndrome, tubulointerstitial disease, and the like), pulmonary diseases (for example, acute pneumonia, pulmonary fibrosis, pulmonary hypertension, chronic obstructive pulmonary disease (COPD), asthma, intractable asthma, systemic inflammatory response syndrome (SIRS), acute lung injury (ALI), acute respiratory distress syndrome (ARDS), sarcoidosis, interstitial pneumonia, hypersensitivity pneumonitis, and the like), pancreatic diseases (for example, diabetes, chronic pancreatitis, and the like), bone diseases (for example, osteoarthritis, rheumatoid arthritis, osteoporosis, bone fractures, bone necrosis, periosteum damage, and the like), diabetic complications (for example, neuropathy, skin ulcers, nephropathy, and the like), dental diseases (for example, periodontal diseases, tooth extraction wounds, oral wound, periodontal tissue damage, and the like), neurological disorders (for example, diabetic neuropathy, spinal canal stenosis, spinal cord injury, amyotrophic lateral sclerosis (ALS), and the like), skin ulcers, pressure sores, hair loss, and the organ and tissue transplantation (for example, liver transplantation, kidney transplantation, lung transplantation, pancreatic islet transplantation, pancreas transplantation, and the like).

As effective substances of the internal regeneration factor production inducing agent of the present invention, one or more arbitrarily selected from the same group of $PGI_2$ agonists may be combined in an appropriate ratio.

Examples of the $PGI_2$ agonist, $EP_2$ agonist, and $EP_4$ agonist that are to be used as the internal regeneration factor production inducing agent of the present invention include $PGE_1$, $PGE_2$, and $PGI_2$, derivatives thereof (for example, 6-oxy-$PGF_1\alpha$, ornoprostil, limaprostil, enprostil, misoprostol, and the like), prodrugs thereof, sustained preparations (sustained-release preparations) thereof (for example, lipo$PGE_1$), and the other internal regeneration factor production inducing agents (for example, a PDE inhibitor, a PPARγ agonist, ARB, and the like), which may be used alone or used in appropriate combination.

The above-described combination of the myocardial support device and the internal regeneration factor production inducing agent of the present invention may be administered as a concomitant drug by combining with another pharmaceutical agent for (1) complementation and/or enhancement of the preventive and/or therapeutic effects of the pharmaceutical agent of the present invention, (2) improving kinetics and absorption of the pharmaceutical agent of the present invention and reducing the dosage thereof, and/or (3) reducing side-effects of the pharmaceutical agent of the present invention.

A concomitant drug of another pharmaceutical agent in the combination of the myocardial support device and the internal regeneration factor production inducing agent, or the integrated myocardial support device of the present invention may be administered in a form of a mixed agent in which both components or the sustained-release preparations are mixed in one preparation thereof, and may be administered in a form of separate preparations. In the case of administering in a form of separate preparations, simultaneous administration or non-simultaneous administration is performed. Also, non-simultaneous administration may be performed by first applying the device of the present invention and then administering another pharmaceutical agent, or by first administering another pharmaceutical agent and then applying the device of the present invention, and administration methods may be the same or different from each other.

Examples of another pharmaceutical agent may include low molecular compounds, and high molecular proteins, polypeptides, polynucleotides (DNA, RNA, and genes), antisenses, decoys, antibodies, an extracellular matrix, and cell adhesion factors, or stem cells, iPS cells, somatic cells, and the like separated from vaccine or tissues. Also, another pharmaceutical agent may be used in intermittent subcutaneous administration or intramuscular administration with repeated oral preparations of the compound 1 or the compound 3, or sustained-release preparations of these compounds (MS). It is possible to appropriately select a dosage of another pharmaceutical agent, using a dose that is used clinically as a standard. Also, mix proportion of the device of the present invention and another pharmaceutical agent can be appropriately selected depending on an age and weight of an administration target, an administration method, administration time, a target disease, a symptom, combination, and the like. For example, 0.01 to 100 parts by mass of another pharmaceutical agent may be used relative to 1 part by mass of the pharmaceutical agent that is combined with the device of the present invention. Another pharmaceutical agent may be administered alone or in combination in an appropriate ratio of two or more arbitrarily selected from the group of the same types and the group of different types indicated below.

There is no particular limitation on diseases for which preventive and/or therapeutic effects are obtained by the above-described concomitant drug as long as diseases complement and/or enhance preventive and/or therapeutic effects of a combination of the myocardial support device and the internal regeneration factor production inducing agent, or of the integrated myocardial support device of the present invention.

Examples of another pharmaceutical agent include antithrombotic agents, circulation-improving agents, smooth muscle dilators, anti-inflammatory agents, local anesthetic agents, analgesic agents, metabolism improving agents, prostaglandins, body regeneration factor proteins, body regeneration factor production genes, various organs stem cells, iPS cells, somatic cells, and the like.

For example, examples of cells include myoblasts, adipocytes, bone marrow cells, myocardial cells, blood cells, mesenchymal stem cells, neural stem cells, hematopoietic stem cells, various types of iPS cells, and the like, which are administered by injections such as intramuscular administration, intravenous administration, and the like, or by attachment of a cell sheet or the like.

Examples of antithrombotic agents include heparin preparations (heparin sodium, heparin calcium, daltepan sodium, and the like), oral anticoagulants (warfarin potassium, and the like), anti-thrombin drugs (gabexate mesilate, nafamostat mesilate, argatroban, and the like), anti-platelet aggregation inhibitors (aspirin, dipyridamole, ticlopidine hydrochloride, beraprost sodium, cilostazol, ozagrel sodium, sarpogrelate hydrochloride, ethyl icosapentate, and the like), thrombolytic agents (urokinase, tisokinase, alteplase, nateplase, monteplase, pamiteplase, and the like), a factor Xa inhibitor, a factor VIIa inhibitor, and the like.

Examples of circulation-improving agents include ifenprodil tartrate, aniracetam, donepezil hydrochloride, amantadine hydrochloride, nicergodine, ibudilast, papaverines, nicotines, calcium antagonists (nifedipine, amlodipine, diltiazepam, azelnidipine, and the like), β-receptor agonists (ephedrine, salbutamol, procaterol, salmeterol, mabuterol, and the like), α-receptor inhibitors (uradipil, terazosin, doxazosin, bunazosin, prazosin, and the like), ARB (losartan, candesartan, valsartan, telmisartan, and the like), PDE inhibitors (theophylline, milrinone, tadalafil, dipyridamole, sildenafil, and the like), and the like.

Examples of local anesthetic agents include steroids, procaine, cocaine hydrochloride, lidocaine hydrochloride, ropivacaine hydrochloride, and the like.

Examples of metabolism improving agents include HMG-CoA reductase inhibitors (for example, atorvastatin, simvastatin, and pravastatin), and the like as hyperlipidemia agents, and as diabetes drugs, PPARγ agonists (for example, thiazolidine derivatives such as pioglitazone and rosiglitazone, adiponectin, leptin, and the like), DPP-IV inhibitors (sitagliptin, vildagliptin, alogliptin, and the like), GLP-1 agonists, and the like.

Examples of analgesic agents include non-steroidal anti-inflammatory drugs (NSAID) such as aspirin, indomethacin, diclofenac, meloxicam, and celecoxib; opioid analgesics such as codeine, morphine, and the like; pentazocine; buprenorphine hydrochloride; eptazocine hydrobromide; and the like.

Examples of prostaglandins include $PGE_1$, $PGE_2$, $PGI_2$, and prodrugs thereof, $lipoPGE_1$, $6$-oxy-$PGF_{1\alpha}$, $6$-oxy-$PGF_{1\alpha}$ derivative, ornoprostil, limaprostil, enprostil, misoprostol, and the like.

Also, examples of the other concomitant drugs that complement and/or enhance preventive and/or therapeutic effects of a combination of the myocardial support device and the internal regeneration factor production inducing agent or the integrated myocardial support device of the present invention include not only concomitant drugs that have been found to date but also concomitant drugs that will be found hereafter, based on the above-described mechanisms, which are usually administered systemically or topically in an oral or parenteral form.

Although the dosage of the internal regeneration factor production inducing agent that is to be administered using a combination of the myocardial support device and the internal regeneration factor production inducing agent or the integrated myocardial support device of the present invention changes depending on the age, weight, symptom, therapeutic effects, administration method, processing time, and the like, the dosage is usually in a range of 1 ng to 1000 mg as an active substance for one adult at a time, and administration is performed by attaching the sustained preparation to the heart once every two weeks, once every four weeks, once every three months, or once to about several times every six months.

Surely, as described above, because the dosage changes depending on various conditions, there is a case in which a less amount than the above-described dosage is sufficient, and there is also a case in which it is necessary to perform administration using the dosage that exceeds the range.

At the time of administration, a concomitant drug of another pharmaceutical agent with the combination of the myocardial support device and the internal regeneration factor production inducing agent of the present invention or the integrated myocardial support device of the present invention is used as an oral solid preparation and an oral liquid preparation for oral administration, or an injection, a subcutaneous/intramuscular injection, an external preparation, a suppository, an inhalant, or a medical device-containing preparation for parenteral administration.

For example, after the combination of the myocardial support device and the compound 1 MS sheet, or the integrated myocardial support device is fitted onto the heart, systemic administration may be performed with repeated oral administration of the compound 1 or subcutaneous/intramuscular injections of the compound 1 MS after loss of sustained-release of the compound 1 MS.

A heart attachment sheet or heart spray of the sustained-release pharmaceutical agent is produced by a formulation that is known or commonly used. For example, the sheet or spray is prepared by adding and suspending the sustained-release pharmaceutical agent containing one or more active substances to/in a bioabsorbable base. The bioabsorbable base for the sheet or spray is selected from known or commonly used bases. For example, the sustained-release pharmaceutical agent may be suspended in a gelatin aqueous solution to produce the sheet, and then the sheet may be dried to prepare a sheet preparation, or the sustained-release preparation may be suspended in a fibrinogen aqueous solution, and then admixed with Ca ions and liquid thrombin, and the obtained mixture may be also administered to affected site by spraying (Beriplast P Combi-Set; CSL Behring, Bolheal; Astellas Pharma Inc., and the like). Also, the sustained-release preparation aqueous suspension may be absorbed by a sheet preparation (Spongel; Astellas Pharma Inc., Gelfoam, Gelfilm; Pfizer Inc., Surgicel; Johnson & Johnson, and the like), the obtained sheet preparation may be encapsulated by fibrin glue (Beriplast P Combi-Set, Bolheal, and the like) or an atelocollagen seal (Integran; Koken Co., Ltd, TachoSil, TachoComb: CSL Behring, and the like).

Moreover, the bioabsorbable base is selected from higher fatty acids or higher fatty acid esters (adipic acid, myristic acid, palmitic acid, stearic acid, oleic acid, adipate, myristate, palmitate, stearate, oleate, and the like), wax (beeswax, spermaceti wax, ceresin, and the like), surfactants (polyoxyethylene alkylether phosphate ester and the like), higher alcohols (cetanol, stearyl alcohol, cetostearyl alcohol, and the like), silicone oils (dimethylpolysiloxane and the like), hydrocarbons (hydrophilic petrolatum, white petrolatum, purified lanolin, liquid paraffin, and the like), glycols (ethylene glycol, diethylene glycol, propylene glycol, polyethylene glycol, macrogol, and the like), vegetable oils (castor oil, olive oil, sesame oil, turpentine oil), animal oils (mink oil, egg yolk oil, squalane, squalene, and the like), gelling agents (carboxymethyl cellulose, hydroxyethyl cellulose, hydroxypropyl cellulose, ethyl cellulose, and the like), surfactants (polyethylene glycol monostearate, and the like), and absorption accelerating agents, which are used alone or in combination. Moreover, the bioabsorbable base may contain a suspending agent (mannitol and the like), a stabilizing agent, an antioxidant (BHT, tocophenol, or the like), and the like.

Also, the heart patch is produced by a known or commonly used formulation. For example, the heart patch is produced by suspending the sustained-release preparations containing one or more active substances in the base, and extending and applying the base onto a support. The patch base is selected from known or commonly used bases. For example, the patch base is selected from high molecular bases, greases, higher fatty acids, tackifiers, and the like, and these are used alone or in combination. Moreover, the patch base may contain an adhesive, amphiphilic dissolution aid agent, permeation accelerating agent, suspending agent, preservative, antioxidant, and the like.

3. Application to Local Site

As organ patch administration of the sustained preparation in the present invention, there is no particular limitation on the administration method as long as the sustained preparation of the pharmaceutical agent of the present invention or the concomitant drug of the sustained preparation of the pharmaceutical agent of the present invention and another pharmaceutical agent is topically supplied to an affected site. For example, a patch, spray, a film, ointment, a sheet, and a medical device-containing preparation in which the medical device (a net, a stent, a suture, a cloth, and the like) contains the sustained preparation of the pharmaceutical agent of the present invention or the concomitant drug of the sustained preparation of the pharmaceutical agent of the present invention and another pharmaceutical agent, a coating preparation that coats a medical device, or a solid preparation such as granules or powders, a patch, a gel, ointment, a film, a preparation encapsulated in a biodegradable polymer, or an encapsulated medical device is used.

It is sufficient that the sustained preparation in the present invention is able to sustainedly supply active substances to an affected site, and there is no limitation thereto. Examples thereof include sustained-release injections (for example, a microcapsule preparation, a microsphere preparation, a nanosphere preparation, and the like), an embedded preparation (for example, a film preparation, a sheet preparation, and the like), ointment, a coating material whose effective substances are contained in or that coats a medical appliance (a stent, a fixing bolt, a surgical suture, or the like), and the like.

The microcapsule preparation, microsphere preparation, and nanosphere preparation in the present invention are minute particle-like preparations that contain active components in a biodegradable polymer, and the active components are gradually released therefrom as a result of the polymer gradually being hydrolyzed in the body.

Regarding to the advanced heart failure treatment material of the present invention, with respect to advanced heart failure such as myocardial infarction, angina pectoris, dilated cardiomyopathy, and the like, for example, using a sheet or spray in which bioabsorbable high-molecular weight compounds are used, the sustained-release preparation of the pharmaceutical agent of the present invention is directly applied to or sprayed on a myocardial ischemia part or the vicinity thereof. Administration is performed by a single dose or multiple doses of spraying or applying to the heart, and the sustained-release preparation is applied for two weeks to six months. More preferably, the sustained-release preparation may be used for two weeks to three months.

One example of a method for applying the advanced heart failure treatment material of the present invention will be described using drawings.

Figure 2:
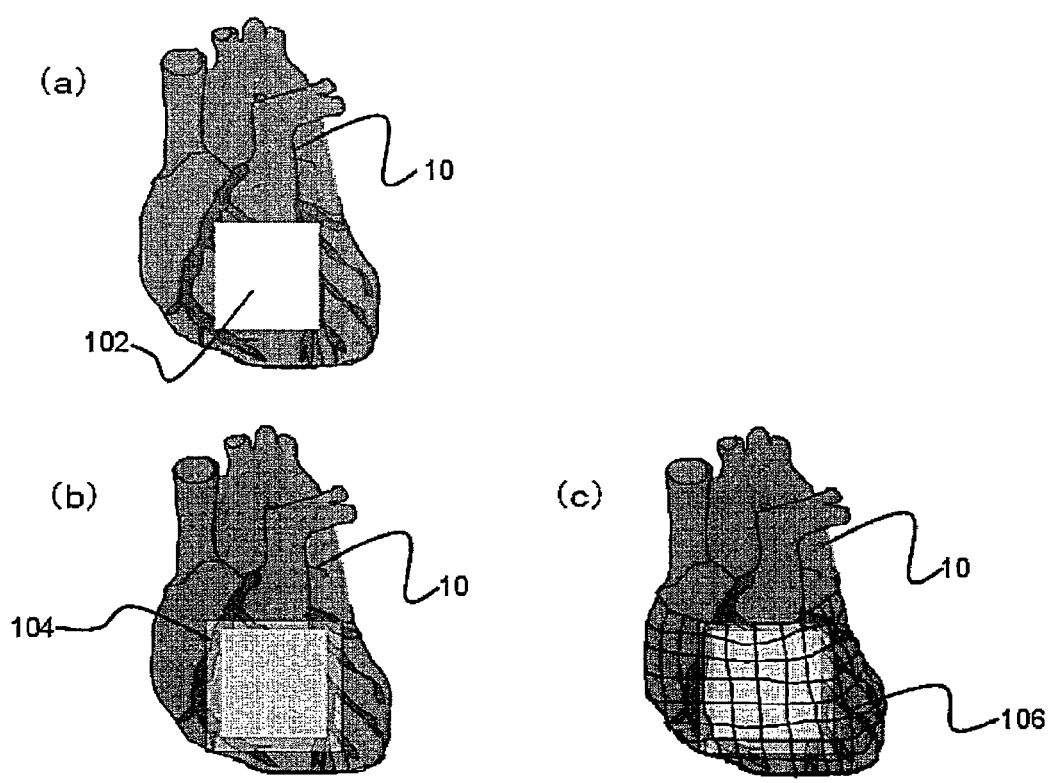
FIG. 2 is a schematic view for illustrating one example, in the case where the advanced heart failure treatment material of the present invention is applied to the human heart, of a procedure of fitting the treatment material thereon.

FIG. 2 is a schematic view for illustrating one example, in the case where the advanced heart failure treatment material of the present invention is applied to the human heart, of a procedure of fitting the treatment material thereon. As shown in FIG. 2(a), a sheet (for example, a gelatin sheet) 102 that is cut in advance into a predetermined shape so as to fit an application range of a heart 10 and contains a predetermined internal regeneration factor production inducing agent in advance is applied to a lower portion (the location is not necessarily limited) of the heart 10, for example. Thereafter, a protecting sheet 104 may be attached thereto in order to protect the sheet 102 as needed. It is desirable that the protecting sheet 104 is designed to be slightly larger than the sheet 102 so as to cover the entire outer surface of the sheet 102. The protecting sheet 104 is also constituted by a material such as a gelatin sheet, for example. Thereafter, as shown in FIG. 2(c), a myocardial support device 106 is mounted so as to further cover the protecting sheet 104 and surround the entire lower portion (a ventricle portion) of the heart 10.

It should be noted that although in the above, the description was mainly given to a case where the advanced heart failure treatment material of the present invention is constituted by a combination of a sustained-release preparation of an internal regeneration factor production inducing agent, a sheet or spray in which bioabsorbable high-molecular weight compounds serving as sustained-release preparation holding agents are used, and the myocardial support device, the present invention is not necessarily limited to this embodiment. In other words, in addition to the combination of the attachment of a sheet or spray in which bioabsorbable high-molecular weight compounds are used, to the heart, and the myocardial support device as described above, the sustained-release preparation of the internal regeneration factor production inducing agent such as the prostaglandin (PG) $I_2$ agonist and the like can be used as prevention and/or treatment material for advanced heart failure by fitting, onto the heart, an integrated myocardial support device obtained by coating the myocardial support device with the sustained-release preparation of the sustained preparation of the $PGI_2$ agonist using a bioabsorbable high-molecular weight compound.

EXAMPLES

Although a method for producing preparations, and pharmacological tests are shown as examples of the present invention hereinafter, this is for well understanding the present invention, and does not limit the scope of the present invention. It should be noted that measurement accuracy and measurement sensitivity of a measurement method for evaluating a compound of the present invention are improved as follows.

Example 1

Production of Sustained Preparation

Preparation Example 1

4-Week Sustained-Release Preparation

A dichloromethane/methanol (1 mL) solution of 100 mg of poly(lactic-co-glycolic acid) (hereinafter, abbreviated to "PLGA") (polylactic acid: glycolic acid=1:1 (mol %), weight average molecular weight 50,000, PLGA5-50, made by Mitsui Chemicals, Inc.) and a compound 1 (25 mg) obtained by using a method described in U.S. Pat. No. 5,480,998 was prepared. The above-described prepared solution was added into 300 mL of 0.1% polyvinyl alcohol (Nacalai Tesque Co., Ltd.) aqueous solution (pH 3.0, adjusted by 1N hydrochloric acid) that was stirred at 5,000 rpm, using TK Robomix (Tokushu Kika Kogyo Co., Ltd., MARK II 2.5 model), the solution was stirred at room temperature for three minutes, to prepare O/W emulsion. This O/W emulsion was stirred at room temperature for two hours, dichloromethane was vaporized, and an oil phase was solidified, and then the residue was centrifuged at 3,000 rpm for ten minutes using a centrifugal separator (Hitachi, 05PR-22). After the supernatant was removed and the mixture was dispersed using distilled water for injection (35 mL), the mixture was centrifuged at 3,000 rpm for 10 minutes using the centrifugal separator. After the supernatant was removed and the residual mixture was dispersed using 0.2% Tween 80 solution (35 mL), the mixture was centrifuged at 3,000 rpm for 10 minutes using the centrifugal separator. After the supernatant was removed and the residual mixture was dispersed using distilled water for injection (35 mL), the mixture was centrifuged at 3,000 rpm for 10 minutes using the centrifugal separator. Finally, the supernatant was removed, the precipitate was immersed in dry ice-methanol and frozen and then dried at reduced pressure, as a result of which a microsphere (MS) preparation of the compound 1 was produced.

As a preparation example 1, the MS preparation having the compound 1 content of 17.1% and a mean particle size of 35.4 μm was obtained. It should be noted that the content and the mean particle size of the compound 1 were measured by the method that will be described later. The same shall apply hereinafter.

Preparation Example 2

2-Week Sustained-Release Preparation

A dichloromethane/methanol (1 mL) solution of 100 mg of poly(lactic-co-glycolic acid) (hereinafter, abbreviated to "PLGA") (polylactic acid: glycolic acid=1:1 (mol %), the weight average molecular weight 20,000, PLGA5020, made by Wako Pure Chemical Industries, Ltd.) and the compound 1 (25 mg) obtained by using the method described in U.S. Pat. No. 5,480,998 was prepared. The subsequent procedures were performed similarly to the preparation example 1 so as to produce a microsphere (MS) preparation of the compound 1.

As a preparation example 2, the MS preparation having the compound 1 content of 18.1% and a mean particle size of 32.6 μm was obtained.

Preparation Example 3

16-Weeks Sustained-Release Preparation

One g of PLA0020 (made by Wako Pure Chemical Industries, Ltd.) and 250 mg of the compound 1 obtained by using the method described in U.S. Pat. No. 5,480,998 were suspended in 10 mL of $CH_2Cl_2$, and 2 mL of methanol was added to dissolve the mixture. This solution was added into 1.5 L of 0.1% (w/v) PVA solution (adjusted to pH 7 using phosphoric acid) that was stirred at 5,000 rpm using Physcotron (Nichion medical science equipment Seisakusho Co., Ltd., a homogenizer NS-60, a generator shaft NS-20), using a pipet near a lateral wing of the shaft to emulsify the solution, as a result of which o/w emulsion was obtained. This o/w emulsion was stirred at room temperature for approximately four hours to vaporize $CH_2Cl_2$ and methanol, and an oil phase was solidified. After the mixture was centrifuged (3,000 rpm, 10 minutes) using the centrifugal separator (Hitachi, himac CR5B2) and the supernatant was removed, the mixture was dispersed using purified water (50 mL) and centrifuged (3,000 rpm, 10 minutes). The supernatant was removed, and the residue was dispersed using 0.2% (w/v) Tween 80 solution (30 mL) and centrifuged (3,000 rpm, 10 minutes). Moreover, the supernatant was further removed, the residue was again dispersed using purified water (30 mL) and centrifuged (3,000 rpm, 10 minutes), and the supernatant was removed, and the residual mixture was frozen using dry ice-methanol and dried at reduced pressure (approximately 12 hours).

As a preparation example 3, the MS preparation having the compound 1 content of 17.9% and a mean particle size of 25.8 μm was obtained.

Preparation Example 4

4-Weeks Sustained-Release Preparation

The MS preparation produced using the above-described Preparation Example 1 was mixed with the MS preparation produced using the preparation example 2 in 1:1 (W/W), and an MS preparation of the compound 1 was produced.

As a preparation example 4, the MS preparation having the compound 1 content of 17.8% and a mean particle size of 31.4 μm was obtained.

Preparation Test Example 1

Encapsulation Efficiency Measurement

An acetonitrile solution containing appropriate internal standard was added to the microspheres produced in Preparation Examples 1, 2, 3, and 4, respectively (approximately 10 mg for each sample) and the mixture was sonicated to dissolve the microspheres. The compound 1 content in each solution was measured by high performance liquid chromatography (HPLC), and the encapsulation efficiency of the compound 1 in the microspheres was calculated by the following equation.

Encapsulation efficiency (%)=(measured content/theoretical content)×100

As a result, the encapsulation efficiency of the microsphere preparations of the preparation examples 1, 2, 3, and 4 was greater than or equal to 70%, and each microsphere preparation had the content of 15% to 20%, and the mean particle size of 25 to 36 μm.

Preparation Test Example 2

In Vitro Release Test, and Particle Size Measurement

The microsphere (MS) preparations produced in Preparation Examples 1, 2, 3, and 4 was weighed to 3 mg (n=3) at each sampling point, and 10 mL of $\frac{1}{15}$ M pH 7 phosphate buffer solution containing 0.2 (w/v) % Tween 80 was added thereto, the mixture was uniformly dispersed by a vortexer (10 seconds) and sonication (20 seconds) and was then left to stand in an isothermal layer of 37° C. Sampling was performed for each container over time, each sample was centrifuged (2,000 rpm, 5 minutes), and then 4 mL of the supernatant and pellets obtained by removing the residual supernatant were cryopreserved.

Ten mL of DMSO was added to the pellets, and the MSs were sufficiently dissolved using a vortexer (10 seconds). Two hundred μL of IS liquid B and 500 μL of a mobile phase (pH 3) were added to 300 μL of this solution, and the solution was sufficiently mixed. Also, similarly, 200 μL of IS liquid B and 500 μL of a mobile phase (pH 3) were added to 300 μL of the supernatant, and the solution was sufficiently mixed. After centrifugation (12,000 rpm, 3 minutes), 10 μL of the supernatant was injected into HPLC.

TABLE 1

| <HPLC conditions> | |
|---|---|
| Apparatus: | Chromatograph (Shimazu LC-10AT), UV detector (Shimazu SPD-10A), data analyzer (Shimazu C-R7A) |
| Detection: | UV-265 nm |
| Column: | SHISEIDO CAPCELLPACK C18 UG120 (4.6 mm i.d × 150 mm) |
| Column temperature: | Constant temperature near 25° C. |
| Mobile phase: | acetonitrile:water:triethylamine = 1000:900:3 (solution of water:triethylamine = 900:3 is adjusted to pH 3 using phosphoric acid) |
| Flow rate: | 1.0 mL/min |
| Internal standard substance (IS): | n-propylparaben |

It should be noted that the particle size was measured by Coulter counter (MultisizerIII, Beckman Coulter, Inc., USA).

Figure 3:
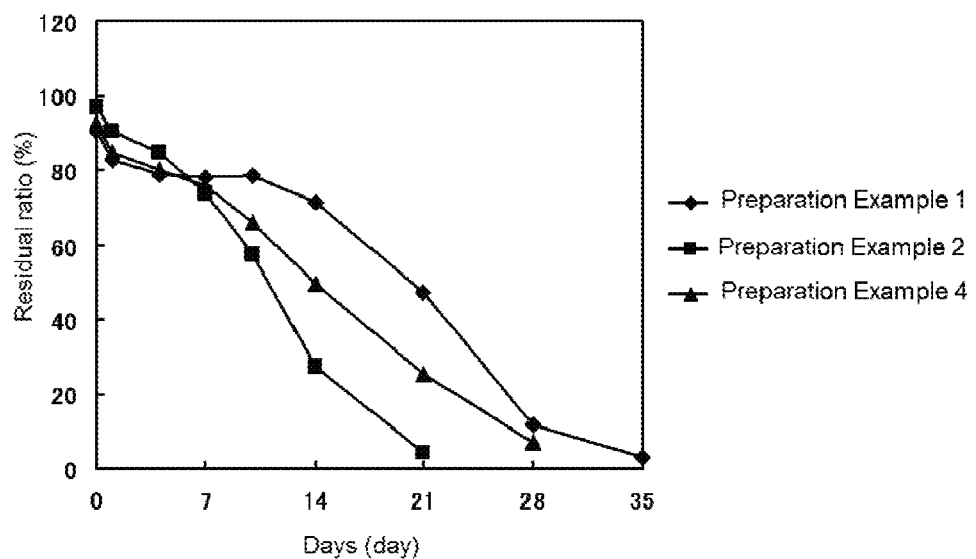
FIG. 3 is a graph showing a result of releasing microsphere preparations produced in preparation examples 1, 2, and 4, and is a graph representing the residual ratio of the drug with respect to days that have elapsed.
Figure 4:
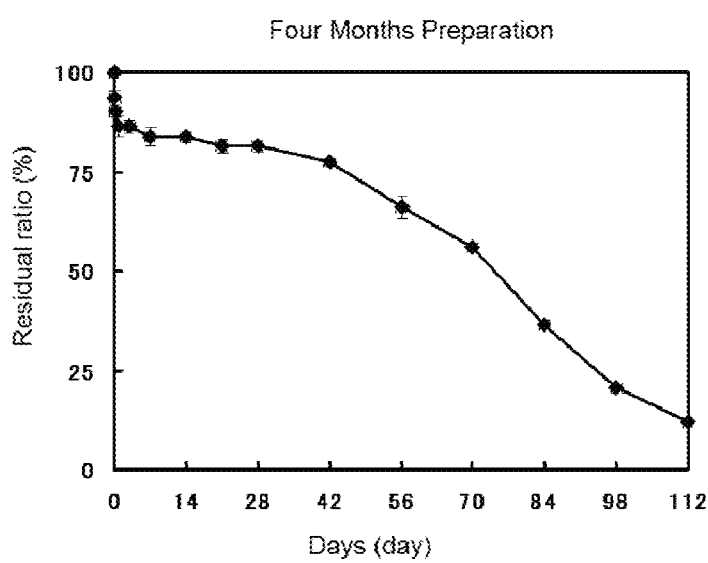
FIG. 4 is a graph showing a result of releasing microsphere preparations produced in a preparation example 3, and is a graph representing the residual ratio of the drug with respect to days that have elapsed.

The release result of microsphere preparations produced in Preparation Examples 1, 2, and 4 is shown in FIG. 3, and the result of microsphere preparation produced in Preparation Example 3 is shown in FIG. 4.

As shown in FIG. 4, the microsphere preparation of the preparation example 3 released 90% or greater of the compound 1 for approximately 4 months. Moreover, as shown in FIG. 3, the microsphere preparation of the preparation examples 1 and 4 released 90% or greater of the compound 1 for approximately 4 weeks.

Preparation Test Example 3

In Vivo Release Test

Blood kinetics were measured using SD male rats (SPF, Japan SLC Inc. (Hamamatsu)). Suspension of the above-described compound 1 amount corresponding to 10 mg (Preparation Examples 1, 2, and 4; 2-week and 4-week release preparations)/kg and 50 mg (Preparation Examples 3; 4-month release preparation)/kg was each administered once to dorsal subcutis using a 23 G disposal injection needle (Terumo) and a disposal syringe for 2.5 mL (Terumo). The dosage of 5 mL/kg was administered. The number of animals in each group was 5.

At each blood collection point, the disposal syringe into which heparin was introduced that was equipped with the 23 G injection needle was used to collect 0.5 mL of blood from a jugular vein, the blood was centrifuged (12,000 rpm, 10 minutes, 4° C.), and then blood plasma was cryopreserved (−30° C.). After tests ended, the concentration of the compound 1 in blood was measured by LC/MS/MS.

TABLE 2

| LC/MS/MS measurement method | |
| --- | --- |
| MS/MS conditions; | |
| MS/MS: | API 4000 |
| Ionization mode: | ESI |
| Ion polarity mode: | Positive |

TABLE 3

| Monitored ions: | | |
| --- | --- | --- |
| Compound | Precursor ion*(m/z) | Product ion*(m/z) |
| Compound 1 | 429.2 | 79.2 |
| Internal substance (IS) | 445.4 | 168.1 |

*Appropriately select value having the strongest ionic strength of m/z ± 0.5 or less with respect to target value.

Figure 5:
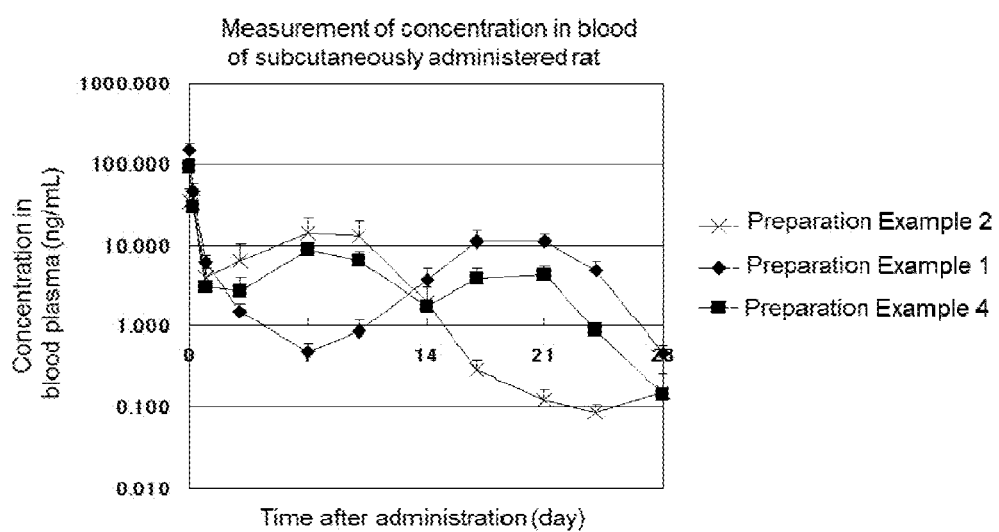
FIG. 5 is a graph showing a result of measuring the concentration of the drug in blood in rats to which the microsphere preparations produced in the preparation examples 1, 2, and 4 have been subcutaneously administered, and is a graph showing a change in the concentration of the drug in blood with respect to time that has elapsed after administration.
Figure 6:
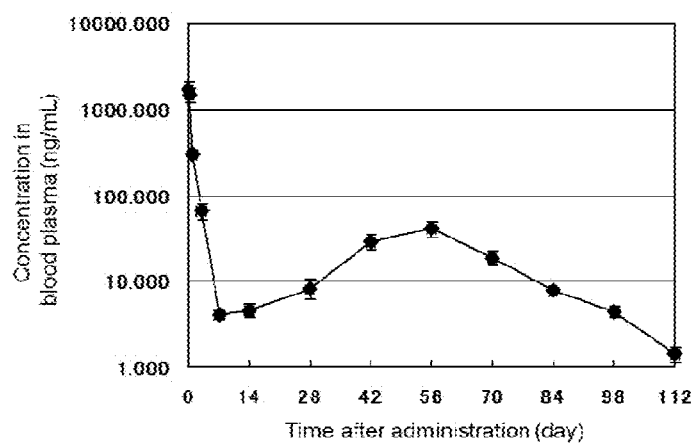
FIG. 6 is a graph showing a result of measuring the concentration of the drug in blood in rats to which the microsphere preparations produced in the preparation example 3 has been subcutaneously administered, and is a graph showing a change in the concentration of the drug in blood with respect to time that has elapsed after administration.

Result; Blood kinetics of Preparation Examples 1, 2, and 4 are shown in FIG. 5. Also, blood kinetics of Preparation Examples 3 are shown in FIG. 6.

Preparation Example 2 showed blood kinetics for about 2 weeks, and Preparation Examples 1 and 4 showed blood kinetics for about 4 weeks (FIG. 5). Also, Preparation Example 3 showed blood kinetics for about 4 months (FIG. 6).

Preparation Example 5

Example for Producing Gelatin Sheet Preparation of Preparation Example 1

After distilled water was added to Gelatin LS-W made by Nitta Gelatin Inc., the mixture was appropriately stirred using a magnetic stirrer to prepare a 2 wt % gelatin aqueous solution. The obtained 2 wt % gelatin aqueous solution was poured in and extended on a petri dish, and was then left to stand in a clean bench and was dried by sending air (abbreviated to "air-dry" hereinafter) at room temperature for approximately 48 hours to obtain a film-like gelatin sheet. The obtained gelatin sheet was subject to dehydrothermal crosslinking treatment under vacuum at 110 to 150° C. for 6 to 24 hours to obtain a water poorly-soluble cross-linked gelatin sheet having a 6 cm square shape.

After introducing 286 mg of Preparation Example 1 to the above-described obtained 2 wt % gelatin aqueous solution, the mixture was appropriately stirred with a magnetic stirrer to obtain a gelatin aqueous solution containing Preparation Example 1 that was uniformly dispersed. The total amount of the obtained gelatin aqueous solution containing Preparation Example 1 was poured in and extended on a petri dish, and was then left to stand in a clean bench and was air-dried at room temperature for approximately 48 hours to obtain a thin film-like gelatin sheet preparation containing Preparation Example 1 having a 5 cm square shape.

The cross-linked gelatin sheet was attached to the gelatin sheet preparation containing Preparation Example 1 using a small amount of water, and was then air-dried for a given time to obtain a two-layered sheet.

Preparation Example 6

Example for Producing Myocardial Support Device (PGA)

Three dimensional data of a canine and human hearts was obtained by a CT scan. Then, heart models that are specific to the canine and human hearts having a three dimensional structure were created by stereo lithography based on the obtained three dimensional data (FIG. 7(a)). Thereafter, a thin film layer having a shape that exactly fits the optically shaped heart models that are specific to the canine and human hearts was described (FIG. 7(b)). Finally, the obtained film was cut and unfolded to obtain a pattern that fits the specific canine and human hearts having a complicated three dimensional shape.

Also, the three dimensional data obtained by a CT scan was directly divided in and expanded to two dimensional data, and pattern data that fits the specific canine and human hearts was obtained without producing a heart model.

Figure 7:
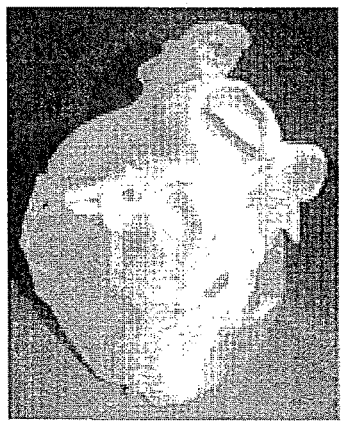
FIG. 7 is a diagram for illustrating the sequential process of producing the myocardial support device using PGA produced in a preparation example 6.
Figure 7:
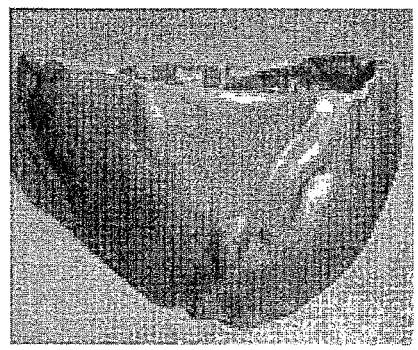
Figure 7:
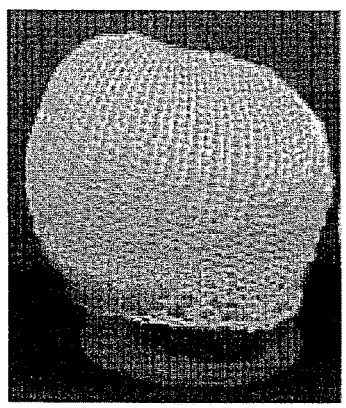
Figure 7:
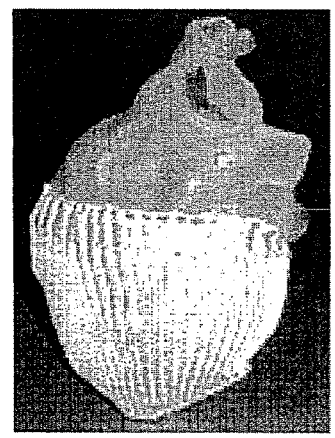

A polyglycolic acid surgical suture 3-0 type made by Gunze Limited (hereinafter, abbreviated to "3-0 PGA suture") was used to obtain a myocardial jacket (a jacket A) that fits the specific shape of canine and human hearts (FIG. 7(c) (for a canine), FIG. 7(d) (for human)) by the three-dimensional seamless wholegarment knitting machine (SWG041 model) made by SHIMA SEIKI MFG., LTD., using the above-described obtained pattern data shown in FIG. 7(b).

Preparation Example 7

Production of Myocardial Support Device (Polyester)

According to the above-described Preparation Example 6, the method described in Japanese Laid-Open Patent Publication No. 2008-161346 was carried out using polyester (a medical surgical suture 6-0 (yarn) of Teflon (registered trademark) coating polyester suture/Shirakawa Co., Ltd.), instead of the polyglycolic acid surgical suture 3-0 type made by Gunze Limited (herein after, abbreviated to "3-0PGA suture"), and a base portion was closed by a seamless computerized flat knitting machine (MACH2-153X15L made by SHIMA SEIKI MFG., LTD.) performing mesh stitch so as to obtain a myocardial jacket.

Preparation Example 8

Production of Integrated Myocardial Support Device

Figure 8:
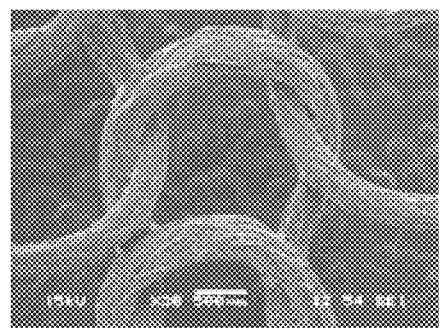
FIG. 8(a) is a photograph that shows the surface state of a device, and that shows that a preparation of the preparation example 1 was fixed on the surface of the device with high dispersiveness by spray application by which a preparation example 1-containing gelatin aqueous solution obtained in the preparation example 5 was sprayed on the device obtained in the preparation example 6.
FIG. 8(b) is a photograph that shows the surface state of the device in the case where gelatin was sprayed thereon at a lower concentration than FIG. 8(a)
FIG. 8(c) is a photograph showing the surface state of the device in the case where gelatin was sprayed thereon at a higher concentration than FIG. 8(a).
Figure 8:
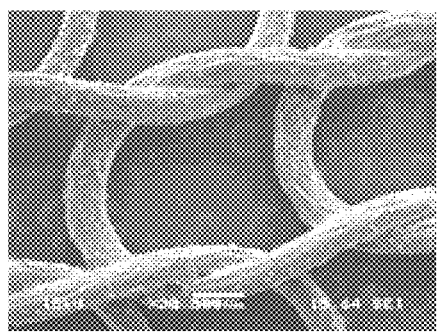
Figure 8:
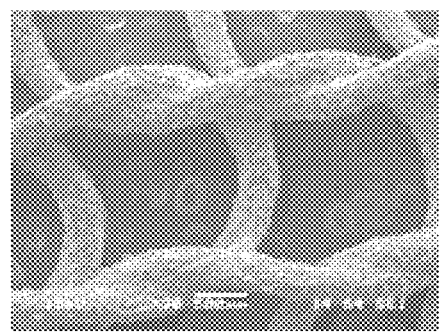

Method; as a result of the earnest studies of a method for directly immobilizing Preparation Example 1 onto the surface of the device obtained in Preparation Example 6, the Preparation Example 1 could be immobilized onto the surface of the Preparation Example 6 so as to have high dispersiveness by spraying the gelatin aqueous solution obtained in Preparation Example 5, containing Preparation Example 1 several times on the device of the Preparation Example 6 (FIG. 8(a)). Thereafter, similarly to Preparation Example 5, the dehydrothermal crosslinking treatment was performed to produce a Preparation Example 1-immobilized myocardial jacket that was coated with a water poorly-soluble gelatin layer.

Moreover, the immobilized amount of the Preparation Example 1 on the surface of the Preparation Example 6 could be controlled by controlling the concentration of the Preparation Example 1 in spray liquid (FIG. 8(b) (low concentration), FIG. 8(c) (high concentration)).

Pharmacological Effect 1; Effectiveness Pharmacological Test Using Canine Coronary Myocardial Ischemia Model Experimental animal: TOYO beagles, female, the body weight of approximately 10 kg, the age of approximately 6 months (Oriental Yeast Co., Ltd.) were used.

Group Structure;

Group 1: untreated group; the chest was reopened, and heart observation time was set to 20 minutes.

Group 2: myocardial support device (preparation example 6) alone group; the myocardial support device alone was fitted onto the heart.

Group 3: compound 1 sustained-release preparation (preparation example 1) alone group; an atelocollagen sheet in which the compound 1 MS was impregnated (the amount of the compound 1 corresponds to 10 mg/kg) was attached to the entire surface of the ventricle, and fixed by 5-0 proline.

Group 4: combination group of myocardial support device (Preparation Example 6) group and compound 1 sustained-release preparation (Preparation Example 1) group; the compound 1 sustained-release preparation (the Preparation Example 1) was suspended in physiological saline (the amount of the compound 1 corresponds to 10 mg/kg), an atelocollagen sheet (Integran; Koken Co., Ltd., two sheets of 50 mm×50 mm) was immersed in the suspension, and the immersed sheets were attached to the heart inside the myocardial support device (the Preparation Example 6).

Group 5: combination group of myocardial support device (Preparation Example 6) group and compound 1 MS Preparation Example 5 (gelatin sheet); after the sheet of the Preparation Example 5 (the amount of the compound 1 corresponds to 10 mg/kg) was attached to the heart, the myocardial support device was fitted thereon over the sheet.

Group 6: combination group of myocardial support device (Preparation Example 6) group and compound 1 MS Preparation Example 3 (16-weeks sustained-release preparation); the compound 1 sustained-release preparation (the Preparation Example 3) was suspended in physiological saline (the amount of the compound 1 corresponds to 30 mg/kg), an atelocollagen sheet (Integran; Koken Co., Ltd., two sheets of 50 mm×50 mm) was immersed in the suspension, and the immersed sheets were attached to the heart inside the myocardial support device (PGA; the Preparation Example 6).

Experimental Method: Blood was collected on the first day, and a cardiac CT scan and echocardiography were performed. Thereafter, the heart was exposed at the left fourth to sixth intercostal opened-chest, an anterior descending coronary artery that ran over the surface of the heart as well as branches were ligated using 5-0 proline to create myocardial infarction. Thereafter, musculus intercostalis were immediately closed by #1 Vicryl, and a surgical incision of subcutis and skin was closed by 2-0 nylon. It should be noted that the cardiac CT scan was performed by using CT Somatom Emotion 16 slice (Siemens AG) to measure the cardiac function.

After 1 week, blood was collected and the cardiac CT scan was performed, and then the incision where the chest was opened on the first day was reopened to perform treatment with each test substance administration. Moreover, after 3 weeks and 5 weeks, blood was collected and a cardiac CT scan was performed. After 8 weeks, blood was also collected and a cardiac CT scan was performed, and then right-left fourth-sixth intercostalis was opened to perform catheterization studies for a left ventricle and a right ventricle. After the studies ended, KCl was directly administered using an injection needle into a right ventricle internal cavity, and the heart was extracted after the heart stopped.

Result: Changes in brain natriuretic peptide (BNP) in blood over time were shown in Table 4, and changes in the cardiac function; left ventricle ejection fraction (LVEF %) were shown in Table 5, as exemplary measurement values. The other measurement items showed similar trends.

According to these results, in the ischemic cardiomyopathy model, compared with the untreated group (Group 1), the myocardial support device (the Preparation Example 6) alone group (Group 2), and the compound 1 sustained-release preparation (the Preparation Example 1) alone group (Group 3) showed significant effect. The combination groups (Groups 4, 5, and 6) of the compound 1 sustained-release preparation (the Preparation Examples 1 and 3) group and the myocardial support device (the Preparation Example 6) group showed extremely significant increase in the effectiveness due to the synergistic effects of each action, compared with each alone (Groups 2 and 3).

It should be noted that the BNP concentration in blood increases as severity of heart failure condition increases. In this model, the concentration increased to approximately 10.7 times in 8 weeks in the untreated group (Group 1), but the concentration increased to approximately 4.5 times in the alone groups (Groups 2 and 3). On the other hand, in the combination groups (Groups 4, 5, and 6), the increase was significantly reduced, that is, the increase in the concentration was 2.8 times. Also, LVEF % is a value that indicates what % of blood is pumped from the left ventricle by one ejection, and decreases as the severity increases. In 8 weeks, a normal (Pre) value; the normal value of 62% was reduced to 43% in the untreated group (Group 1), and the value indicated the advanced heart failure condition, but LVEF % was about 50% and it was improved in the alone groups (Groups 2 and 3). On the other hand, LVEF % was further improved to 54% in the combination groups (Groups 4, 5, and 6), and the effect was significant.

TABLE 4

BNP (pmol/L)

|  | Group 1; untreated | Group 2; net only | Group 3; compound 1 MS Preparation Example 1 (atelocollagen) | Group 4; net + compound 1 MS Preparation Example 1 (atelogollagen) combination group | Group 5; net + compound 1 MS Preparation Example 5 (gelatin) combination group | Group 6; net + compound 1 MS Preparation Example 3 (atelocollagen) combination group |
|---|---|---|---|---|---|---|
| Normal (PreMI) | 159.0 ± 65.3 | 178.0 ± 67.2 | 260.0 ± 83.2 | 202.0 ± 83.2 | 188.1 ± 70.2 | 200.1 ± 55.5 |
| Before treatment | 867.6 ± 197.0 | 964 ± 112.9 | 969.8 ± 105.2 | 928.6 ± 183.6 | 933.1 ± 201.2 | 899.9 ± 109.3 |
| 3 W | 1202.8 ± 399.0 | 719.8 ± 169.0 | 1030.8 ± 165.2 | 772.2 ± 174.2 | 788.1 ± 80.2 | 918.4 ± 101.3 |
| 5 W | 1090.4 ± 259.6 | 850 ± 152.5 | 694.6 ± 102.5 | 905.8 ± 91.0 | 782.4 ± 77.5 | 823.9 ± 100.2 |
| 8 W | 1708.8 ± 180.7 | 889.2 ± 80.2 | 1012.8 ± 144.3 | 559.8 ± 91.2 | 588.1 ± 123.2 | 488.1 ± 80.4 |

"Before treatment" refers to value just before treatment one week after myocardial infarction.

TABLE 5

LVEF %

|  | Group 1; untreated | Group 2; net only | Group 3; compound 1 MS preparation example 1 (atelocollagen) | Group 4; net + compound 1 MS preparation example 1 (atelocollagen) combination group | Group 5; net + compound 1 MS preparation example 5 (gelatin) combination group | Group 6; net + compound 1 MS preparation example 3 (atelocollagen) combination group |
|---|---|---|---|---|---|---|
| Normal (PreMI) | 62.0 ± 2.1 | 59.0 ± 1.2 | 61.5 ± 2.5 | 61.0 ± 3.4 | 62.1 ± 1.8 | 60.5 ± 2.2 |
| Before treatment | 46.4 ± 2.1 | 45.1 ± 1.3 | 44.7 ± 2.7 | 45.1 ± 2.0 | 45.3 ± 2.0 | 44.8 ± 1.6 |
| 3 W | 46.6 ± 3.1 | 47.2 ± 1.0 | 49.1 ± 2.0 | 50.0 ± 1.5 | 49.3 ± 1.6 | 50.4 ± 2.0 |
| 5 W | 42.3 ± 1.6 | 52.6 ± 1.6 | 48.6 ± 1.7 | 53.7 ± 2.4 | 54.1 ± 1.2 | 53.7 ± 2.4 |
| 8 W | 43.2 ± 2.4 | 50.16 ± 0.3 | 50.5 ± 0.7 | 54.3 ± 1.5 | 53.9 ± 2.2 | 54.2 ± 1.9 |

"Before treatment" refers to value just before treatment one week after myocardial infarction.

Pharmacological Effect 2; Effectiveness Pharmacology Using Canine High Speed Pacing (Dilated Cardiomyopathy) Model Experimental animal: TOYO beagles, female, the body weight of approximately 10 kg, the age of approximately 6 months (Oriental Yeast Co., Ltd.) were used.

Group Structure;

Group 1; untreated group,

Group 2; atelocollagen sheet of compound 1 obtained in preparation example 3 alone group, Group 3; myocardial support device (polyester) of preparation example 7 alone group, and Group 4; combination administration group of these ones (Groups 2 and 3).

Test Method and Evaluation: A cardiac CT scan and echocardiography were performed on the first day. Thereafter, the heart was exposed at left fourth to sixth intercostal opened-chest, a pacemaker lead was placed at the free wall of the right ventricle and connected to a pacemaker (Taisho Biomed Instruments Co., Ltd., experimental implantable pacemaker TNT series) placed under subcutis near the skin incision, and then at the same time, treatment by any one of the above-described Groups 1, 2, 3, and 4 was performed. Thereafter, immediately, pacing was started at approximately 200/minute, musculus intercostalis were immediately closed by #1 Vicryl, and a surgical incision of subcutis and skin was closed by 2-0 nylon.

After 4 weeks, a cardiac CT scan and cardiac catheterization were performed to measure the cardiac function. CT Somatom Emotion 16 slice (Siemens AG) was used for measurement by the cardiac CT scan.

Result; As shown in Tables 6 and 7, also in the dilated cardiomyopathy model, compared with the untreated group (Group 1), the alone groups of the preparation example 3 (Group 2) and the preparation example 7 (Group 3) each showed effect in both cardiac function; LVEF (left ventricle ejection fraction; %) and Ees (cardiac contractility). The group combined these (Group 4) showed significant increase in the usefulness due to the synergistic effects of each action, compared with each single-element group.

TABLE 6

|  | LVEF (left ventricle ejection fraction) (%) | | Difference in LEEF |
|---|---|---|---|
|  | Zeroth week | Forth week |  |
| Untreated group (Group 1) | 61.1 | 33.8 | Δ27.3 |
| Preparation Example 3 (Group 2) | 56.3 | 40.4 | Δ15.9 |
| Preparation Example 7 (Group 3) | 58.9 | 42.8 | Δ16.1 |
| Combination group (Group 4) | 61.3 | 47.9 | Δ13.4 |

TABLE 7

|  | Ees (cardiac contractility) |
|---|---|
| Untreated group (Group 1) | 2.7 |
| Preparation Example 3 (Group 2) | 5.3 |
| Preparation Example 7 (Group 3) | 5.8 |
| Combination group (Group 4) | 6.7 |

INDUSTRIAL APPLICABILITY

The present invention is useful for the prevention and/or treatment of advanced heart failures, for example, associated with dilated cardiomyopathy, severe ischemic cardiomyopathy, or the like as a cell-free cardiovascular/myocardial regeneration therapy that is an alternative to a heart transplantation, artificial hearts, and a cell transplantation therapy. Also, the present invention is useful for the prevention and/or treatment of chronic rejection associated with a heart transplantation, congestive cardiac failure, right heart failure resulting from pulmonary hypertension and the like, diastolic heart failure, and the like.

REFERENCE LIST

Heart 10
Myocardial support device 100, 106
Sheet 102
Protecting sheet 104

The invention claimed is:

1. An advanced heart failure treatment material comprising a pharmaceutical agent, an agent holding the pharmaceutical agent, and a myocardial support device,
   wherein the pharmaceutical agent is an internal regeneration factor production inducing agent comprising a prostaglandin $I_2$ agonist indicated by the following general Formula (I) or a salt thereof:

Formula (1)

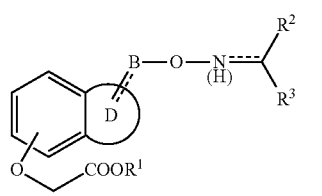
(I)

in Formula (I), 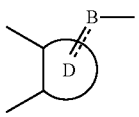 is

 (i)

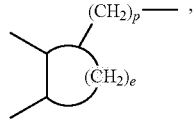 (ii)

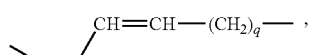 (iii)

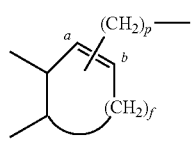 or

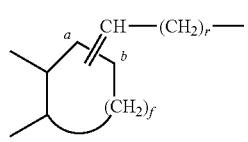 (iv)

wherein,
   $R^1$ is a hydrogen atom or a C1-4 alkyl group,
   $R^2$ is (i) a hydrogen atom, (ii) a C1-8 alkyl group that may be branched or form a ring, (iii) a phenyl group or a C4-7 cycloalkyl group, (iv) a 4-7-membered single ring containing one nitrogen atom, (v) a C1-4 alkyl group substituted by a benzene ring or a C4-7 cycloalkyl group, or (vi) a C1-4 alkyl group substituted by a 4-7-membered single ring containing one nitrogen atom,
   $R^3$ is (i) a C1-8 alkyl group that may be branched or form a ring, (ii) a phenyl group or a C4-7 cycloalkyl group, (iii) a 4-7-membered single ring containing one nitrogen atom, (iv) a C1-4 alkyl group substituted by a benzene ring or a C4-7 cycloalkyl group, or (v) a C1-4 alkyl group substituted by a 4-7-membered single ring containing one nitrogen atom, and
   e is an integer of 3-5, f is an integer of 1-3, p is an integer of 1-4, q is 1 or 2, and r is an integer of 1-3,
   provided that in a case where, is a group indicated by (iii) or (iv), —$(CH_2)_p$— and =CH—$(CH_2)_r$— are bound to a or b on a ring, and a ring in $R^2$ and $R^3$ may be substituted by one to three C1-4 alkyl groups, C1-4 alkoxy groups, halogen atoms, nitro groups, or trihalomethyl groups,
   wherein the agent holding the pharmaceutical agent comprises at least one high-molecular weight compound selected from the group consisting of fibrin, gelatin, collagen, and hyaluronic acid.

2. The advanced heart failure treatment material according to claim 1, wherein the internal regeneration factor production inducing agent is in a sustained-release preparation.

3. The advanced heart failure treatment material according to claim 1, wherein the agent holding for the pharmaceutical agent is a sustained-release preparation holding agent.

4. The advanced heart failure treatment material according to claim 2, wherein the sustained-release preparation of the internal regeneration factor production inducing agent constitutes a sheet or spray together with the sustained-release preparation holding agent.

5. The advanced heart failure treatment material according to claim 4, wherein the sustained-release preparation of the internal regeneration factor production inducing agent is coated onto the myocardial support device via the sustained-release preparation holding agent.

6. The advanced heart failure treatment material according to claim 1, wherein the high-molecular weight compound is at least one natural high-molecular weight compound selected from the group consisting of fibrin, atelocollagen, and gelatin.

7. The advanced heart failure treatment material according to claim 2, wherein the sustained-release preparation of the internal regeneration factor production inducing agent is produced using a biodegradable high-molecular weight compound.

8. The advanced heart failure treatment material according to claim 1, wherein the prostaglandin $I_2$ agonist is (E)-[5-[2-[1-phenyl-1-(3-pyridyl)methylideneaminoxy]ethyl]-7,8-dihydronaphthalen-1-yloxy]acetic acid or salt thereof.

9. The advanced heart failure treatment material according to claim 1, wherein the internal regeneration factor production inducing agent is a sustained-release preparation of (E)-[5-[2-[1-phenyl-1-(3-pyridyl)methylideneaminoxy]ethyl]-7,8-dihydronaphthalen-1-yloxy]acetic acid.

10. The advanced heart failure treatment material according to claim 9, wherein the internal regeneration factor production inducing agent is a microsphere (MS) preparation of (E)-[5-[2-[1-phenyl-1-(3-pyridyl)methylideneaminoxy]ethyl]-7,8-dihydronaphthalen-1-yloxy]acetic acid.

11. The advanced heart failure treatment material according to claim 10, wherein the microsphere preparation is constituted by polylactic acid, polyglycolic acid, or poly(lactic-co-glycolic acid) or a mixture thereof or a hydrogel.

12. The advanced heart failure treatment material according to claim 11, wherein the biodegradable high-molecular weight compound is constituted by polylactic acid, or polyglycolic acid, poly(lactic-co-glycolic acid) having a weight average molecular weight of 5,000 to 50,000, or a mixture thereof, or a hydrogel.

13. The advanced heart failure treatment material according to claim 10, wherein the microsphere preparation has a drug content from 15 to 20% and a mean particle size from 25 to 36 μm.

14. The advanced heart failure treatment material according to claim 1, wherein the myocardial support device is constituted by at least one high-molecular weight compound selected from the group consisting of polyester, aromatic polyamide fiber, polyglycolic acid, polylactic acid, and polydioxanone.

15. The advanced heart failure treatment material according to claim 14, wherein the myocardial support device is constituted by at least one high-molecular weight compound selected from the group consisting of polyester or polyglycolic acid.

16. The advanced heart failure treatment material according to claim 1, comprising the internal regeneration factor production inducing agent constituted by a microsphere preparation of (E)-[5-[2-[1-phenyl-1-(3-pyridyl)methylideneaminoxy]ethyl]-7,8-dihydronaphthalen-1-yloxy]acetic acid, the sustained-release preparation holding agent constituted by fibrin, atelocollagen, or gelatin, and the myocardial support device constituted by a polyester surgical suture or a polyglycolic acid surgical suture.

17. The advanced heart failure treatment material according to claim 16, comprising an atelocollagen sheet that is impregnated with a microsphere preparation of (E)-[5-[2-[1-phenyl-1-(3-pyridyl)methylideneaminoxy]ethyl]-7,8-dihydronaphthalen-1-yloxy]acetic acid or a gelatin sheet that is impregnated with the microsphere preparation, and a myocardial support device constituted by a polyester surgical suture or a polyglycolic acid surgical suture.

18. The advanced heart failure treatment material according to claim 16, which is constituted by spraying an atelocollagen aqueous solution containing a microsphere preparation of (E)-[5-[2-[1-phenyl-1-(3-pyridyl)methylideneaminoxy]ethyl]-7,8-dihydronaphthalen-1-yloxy]acetic acid, a gelatin aqueous solution containing the microsphere preparation, or a fibrin aqueous solution containing the microsphere preparation on the myocardial support device constituted by a polyester surgical suture or a polyglycolic acid surgical suture.

19. The advanced heart failure treatment material according to claim 1, which is used for treatment of dilated cardiomyopathy, advanced ischemic cardiomyopathy, inflammatory cardiomyopathy, chronic rejection associated with a heart transplantation, congestive heart failure, right heart failure resulting from pulmonary hypertension and the like, or diastolic heart failure.

20. The advanced heart failure treatment material according to claim 1, which is fitted externally onto a heart of a mammal.

* * * * *

UNITED STATES PATENT AND TRADEMARK OFFICE
CERTIFICATE OF CORRECTION

| | |
|---|---|
| PATENT NO. | : 9,597,436 B2 |
| APPLICATION NO. | : 14/429565 |
| DATED | : March 21, 2017 |
| INVENTOR(S) | : Yoshiki Sawa et al. |

Page 1 of 1

It is certified that error appears in the above-identified patent and that said Letters Patent is hereby corrected as shown below:

In the Claims

Column 38, Line 45, Claim 3, after "holding" delete "for"

Signed and Sealed this
Eighteenth Day of July, 2017

Joseph Matal
*Performing the Functions and Duties of the*
*Under Secretary of Commerce for Intellectual Property and*
*Director of the United States Patent and Trademark Office*